(12) United States Patent
Hitoshi et al.

(10) Patent No.: US 7,413,870 B2
(45) Date of Patent: Aug. 19, 2008

(54) SAK: MODULATION OF CELLULAR PROLIFERATION FOR TREATMENT OF CANCER

(75) Inventors: Yasumichi Hitoshi, Mountain View, CA (US); Susan Demo, Sunnyvale, CA (US); Yonchu Jenkins, San Francisco, CA (US)

(73) Assignee: Rigel Pharmaceuticals, Incorporated, South San Francisco, CA (US)

( * ) Notice: Subject to any disclaimer, the term of this patent is extended or adjusted under 35 U.S.C. 154(b) by 223 days.

(21) Appl. No.: 10/026,021

(22) Filed: Dec. 21, 2001

(65) Prior Publication Data

US 2003/0027756 A1 Feb. 6, 2003

Related U.S. Application Data

(60) Provisional application No. 60/309,632, filed on Aug. 1, 2001.

(51) Int. Cl.
*C12Q 1/50* (2006.01)
(52) U.S. Cl. ....................................... 435/15
(58) Field of Classification Search ............... 435/5, 435/6, 7.1
See application file for complete search history.

(56) References Cited

U.S. PATENT DOCUMENTS

| | | | | |
|---|---|---|---|---|
| 5,589,356 A | * | 12/1996 | Tam | 435/68.1 |
| 5,650,501 A | | 7/1997 | Dennis et al. | |
| 5,959,081 A | * | 9/1999 | Lecka-Czernik | 530/358 |
| 5,976,893 A | | 11/1999 | Dennis et al. | |
| 6,569,662 B1 | | 5/2003 | Tang et al. | |

FOREIGN PATENT DOCUMENTS

WO   WO 01/53312 A1 * 7/2001

OTHER PUBLICATIONS http://www.m-w.com/cgi-bin/dictionary?book=Dictionary&va=antisense*
Kam et al., "Human SAK related to the PLK/polo family of cell cycle kinases shows high mRNA expression in testis," *Oncology Reports* 4: 505-510 (1997).
Chaturvedi et al., "Mammalian Chk2 is a downstream effector of the ATM-dependent DNA damage checkpoint pathway," *Oncogene* 18: 4047-4054 (1999).
Brown et al., "A human Cds 1-related kinase that functions downstream of ATM protein in the cellular response to DNA damage," *Proc. Natl. Acad. Sci. USA* 96: 3745-3750 (1999).
Blasina et al., "A human homologue of the checkpoint kinase Cds 1 directly inhibits Cdc25 phosphatase," *Current Biology* 9: 1-10 (1998).
Hudson et al., "Late mitotic failure in mice lacking Sak, a polo-like kinase," *Current Biology* 11: 441-446 (2001).
Glover et al., "Polo-like kinases: a team that plays throughout mitosis," *Genes & Dev.* 12: 3777-3787 (1998).
Hudson et al., "Sak kinase gene structure and transcriptional regulation," *Gene* 241: 65-73 (2000).
Matsuoka et al., "Linkage of ATM to Cell Cycle Regulation by the Chk2 Protein Kinase," *Science* 282: 1896-1897 (1998).
Fode, C., et al., "Sak, a murine protein-serine/threonine kinase that is related to the *Drosophila* polo kinase and involved in cell proliferation," *Proc. Natl. Acad. Sci. USA* Jul. 1994, vol. 91, pp. 6388-6392.
Fode, Carol, et al., "Constitutive Expression of Murine Sak-a Suppresses Cell Growth and Induces Multinucleation," *Molecular and Cellular Biology*, 1996, vol. 16, No. 9, pp. 4665-4672.
Hirao, Atsushi, et al. "DNA Damage-Induced Activation of p53 by the Checkpoint Kinase Chk2," *Science*, 2000, vol. 287, pp. 1824-1827.
Karn, Thomas, et al., "Human SAK related to the PLK/polo family of cell cycle kinases shows high mRNA expression in testis," *Oncology Reports*, 1997, vol. 4, pp. 505-510.
Lukas, Claudia, et al., "DNA Damage-activated Kinase Chk2 Is Independent of Proliferation or Differentiation Yet Correlates with Tissue Biology," *Cancer Research*, 2001, vol. 61, pp. 4990-4993.
MacMillan, Jennifer C., et al., "Comparative Expression of the Mitotic Regulators SAK and PLK in Colorectal Cancer," *Annals of Surgical Oncology*, vol. 8, No. 9, pp. 729-740, Oct. 2001.

* cited by examiner

*Primary Examiner*—Misook Yu
(74) *Attorney, Agent, or Firm*—Klarquist Sparkman, LLP

(57) ABSTRACT

The present invention relates to regulation of cellular proliferation. More particularly, the present invention is directed to nucleic acids encoding SAK, which is a protein kinase involved in modulation of cellular proliferation and cell cycle regulation. The invention further relates to methods for identifying and using agents, including small molecule chemical compositions, antibodies, peptides, cyclic peptides, nucleic acids, RNAi, antisense nucleic acids, and ribozymes, that modulate cell cycle regulation and cellular proliferation via modulation of SAK; as well as to the use of expression profiles and compositions in diagnosis and therapy related to cell cycle regulation and modulation of cellular proliferation, e.g., for treatment of cancer and other diseases of cellular proliferation.

9 Claims, 19 Drawing Sheets

Figure 1

```
ATGGACCATGCTAATGAGGGTCATCGTATTTGTTTAGCACTGGAATCCATAAT
TTCAGAAGAGGAAAGGAAAACTAGGAGTGCTCCCTTTTCCCAATAATCATA
GGAAGAAAACCTGGTAGTACTAGTTCACCTAAGGCCTTATCACCTCCTCCTTC
TGTGGATTCAAATTACCCAACGAGAGATAGAGCATCTTTCAACAGAATGGTC
ATGCATAGTGCTGCTTCTCCAACACAGGCACCAATCCTTAATCCCTCTATGGT
TACAAATGAAGGACTTGGTCTTACAACTACAGCTTCTGGAACAGACATCTCTT
CTAATAGTCTAAAAGATTGTCTTCCTAAATCAGCACAACTTTTGAAATCTGTT
TTTGTGAAAAATGTTGGTTGGGCTACACAGTTAACTAGTGGAGCTGTGTGGGT
TCAGTTTAATGATGGGTCCCAGTTGGTTGTGCAGGCAGGAGTGTCTTCTATCA
GTTATACCTCACCAAATGGTCAAACAACTAGGTATGGAGAAAATGAAAAATT
ACCAGACTACATCAAACAGAAATTACAGTGTCTGTCTTCCATCCTTTTGATGT
TTTCTAATCCGACTCCTAATTTTCATTGA

>SAK amino acid seq. (SEQ ID NO:2)

MATCIGEKIEDFKVGNLLGKGSFAGVYRAESIHTGLEVAIKMIDKKAMYKAGMV
QRVQNEVKIHCQLKHP
SILELYNYFEDSNYVYLVLEMCHNGEMNRYLKNRVKPFSENEARHFMHQIITGM
LYLHSHGILHRDLTLS
NLLLTRNMNIKIADFGLATQLKMPHEKHYTLCGTPNYISPEIATRSAHGLESDVW
SLGCMFYTLLIGRPP
FDTDTVKNTLNKVVLADYEMPSFLSIEAKDLIHQLLRRNPADRLSLSSVLDHPFM
SRNSSTKSKDLGTVE
DSIDSGHATISTAITASSSTSISGSLFDKRRLLIGQPLPNKMTVFPKNKSSTDFSSSG
DGNSFYTQWGNQ
ETSNSGRGRVIQDAEERPHSRYLRRAYSSDRSGTSNSQSQAKTYTMERCHSAEM
LSVSKRSGGGENEERY
SPTDNNANIFNFFKEKTSSSSGSFERPDNNQALSNHLCPGKTPFPFADPTPQTETV
QQWFGNLQINAHLR
KTTEYDSISPNRDFQGHPDLQKDTSKNAWTDTKVKKNSDASDNAHSVKQQNTM
KYMTALHSKPEIIQQEC
VFGSDPLSEQSKTRGMEPPWGYQNRTLRSITSPLVAHRLKPIRQKTKKAVVSILD
SEEVCVELVKEYASQ
EYVKEVLQISSDGNTITIYYPNGGRGFPLADRPPSPTDNISRYSFDNLPEKYWRKY
QYASRFVQLVRSKS
PKITYFTRYAKCILMENSPGADFEVWFYDGVKIHKTEDFIQVIEKTGKSYTLKSES
EVNSLKEEIKMYMD
HANEGHRICLALESIISEEERKTRSAPFFPIIIGRKPGSTSSPKALSPPPSVDSNYPTR
DRASFNRMVMH
SAASPTQAPILNPSMVTNEGLGLTTTASGTDISSNSLKDCLPKSAQLLKSVFVKNV
GWATQLTSGAVWVQ
FNDGSQLVVQAGVSSISYTSPNGQTTRYGENEKLPDYIKQKLQCLSSILLMFSNPT
PNFH
```

Alignment of the Kinase Domain of SAK with Other Mitotic Kinases

```
                10         20         30         40         50         60         70         80         90        100
                 |          |          |          |          |          |          |          |          |          |
hSAK    ------------------------------------------------------------------------------MEPAAG-FLSPRPFQR-------TAAATAPPAGPGPPPSALRGPELEMLAGLPTSDP
hFNK    ---------------------------------------MELLRTITYQPAASTKMCEQALGKGCGDSKKKRPPQPPEESQPPQSQAQVPPAPHHHHHSHS
hSNK    ----------------------------------MSAAVT-------AGKLAR--------APAD-PGKAGVPGVAAPG--APAAAPPAKEI
hPLK1   MDRSKENCISGPVKATAPVGGPKRVLVTQQFPCQNPLPVNSGQAQRVLCPSNSSQRIPLQAQKLVSSHKPVQNQKQKQLQQTSVPHPVSRPLNNTQKSKQ
hARK    ------------------------------------------------------------------------------------------MATCI 110        120        130        140        150        160        170        180        190        200
                 |          |          |          |          |          |          |          |          |          |
hSAK    G-----------------------EKIEDFKVGNLLGKGSFAGVYRAESIHTGLEVAIKMIDKKAMYKAGMVQRVKNEVKIHCQLKHPSILELYNYF
hFNK    G-----------------------RLITDPRSGRTYLKGRLLGKGGFARCYEATDTETGSAYAVKVIPQSRVVKPHQREKILNEIELHRDLQHRHIVRFSHHF
hSNK    GPEIS-------------------RIIVDPTTGKRYCRGKVLGKGGFAKCYEMTDLTNNKVYAAKIIPHSRVAKPHQREKIDKEIELHRILHHKHVVQFYHYF
hPLK1   P-------------------EVLVDPRSRRRYVRGRFLGKGGFAKCFEISDADTKEVFAGKIVPKSILLLKPHQREKMSMEISIHRSLAHQHVVGFHGFF
hARK    PLPSAPENNPEEELASKQKNEESKKRQWALEDFEIGRPLGKGKFGNVYLAREKQSKGILALKVLFKAQLEKAGVEHQLRREVEIQSHLRHPNILRLYGYF
                                                                                                        *
                210        220        230        240        250        260        270        280        290        300
                 |          |          |          |          |          |          |          |          |          |
hSAK    EDSNYYVYLVLEMCHNGEMNRYLKNRVKPFSENEARHFMHQIITGMLYLHSHGIILHRDLTLSNLLLTRNMNIKIADFGLATQLKMPHEKHYTLCGTPNYIS
hFNK    EDADNIYIFLELCSRKSLAHIWK-ARHTLLEPEVRYYLRQILSGLKYLRQILSGLKYLHEQEILHRDLKLGNFFITENMELKVGDFGLAARLEPPEQRKKTICGTPNYVA
hSNK    EDKENIYILLEYCSRRSMAHILK-ARKVLTEPEVRYYLRQIVSGLKYLHEQEILHRDLKLGNFFINEAMELKVGDFGLAARLEPLEHRRTICGTPNYLS
hPLK1   EDNDFVFVVLELCRRRSLLELHK-RRKALTEPEARYYLRQIVLGCQYLHRNRVIHRDLKLGNLFLNEDLEVKIGDFGLATKVEYDGERKKTLCGTPNYIA
hARK    HDATRVYLILEYAPLGTVYRELQ-KLSKFDEQRTATYITELANALSYCHSKRVIHRDIKPENLLLGSAGELKIADFGWS--VHAPSSRRTTLCGTLDYLP
          *          **                 *  :    *   ****:               :       **      ****  :       :**  :
                310        320        330        340        350        360        370        380        390        400
                 |          |          |          |          |          |          |          |          |          |
hSAK    PEIATRSAHGLESDVWSLGCMFYTLLIGRPPFDTDTVKNTLNKVVLADYEMPTFLSIEAKDLIHQLLRRNPADRLSLSSVLDHPFMSRNSSTKSKDLGTV
hFNK    PEVLLRQGHGPEADVWSLGCVMYTLLCGSPPFETADLKETYRCIKQVHYTLPASLSLPARQLLAAILRASPRDRPSIDQILRHDFFTK-------GYT
hSNK    PEVLNKQGHGCESDIWALGCVMYTMLLGRPPFETTNLKETYRCIREARYTMPSSLLAPAKHLIASMLSKNPEDRPSLDDIIRHDFFLQ-------GFT
hPLK1   PEVLSKKGHSFEVDVWSIGCIMYTLLVGKPPFETSCLKETYLRIKKNEYSIPKHINPVAASLIQKMLQTDPTARPTINELLNDEFFTS-------GYI
hARK    HDEKVDLMSLGVLCYEFLVGKPPFEANTYQETYKRISRVEFTFPDFVTEGARDLISRLLKHNPSQRPMLREVLEHPWITAN
         **    *  *  **:*  *  **

410        420        430        440        450        460        470        480        490        500
                 |          |          |          |          |          |          |          |          |          |
hSAK    EDSIDSGHATISTAITASSSTSISGSLFDKRRLLIGQPLPNKMTVFPKNKSSTDFSSSGDGNSFYTQWGNQETSNSGRGRVIQDAEERPHSRYLRRAYSS
hFNK    PDRLPISSCVTVPDLITPPNP---ARSLFAKV-------TKSLFVRKKK--------------SKNHAQERDE-------VSGLVS
hSNK    PDRLSSCCHTVPDFHLSSP---AKNFFKKA---------AAALFGGKKDKARYI---------DTHNRVSKEDED-----IYKLRH
hPLK1   PARLPITCLTIPPRFSIAPS---SLDPSNRK--------PLTVLNKGLEN-----------PLPERPREKEEP------VVRETG
hARK    -SSKPSNCQNKESASKQS--
```

Two hSAK Mutants Generated for the Dominant negative Studies: D154A and K41M

FIG. 2.

Summary of Target Validation Studies: SAK

Dominant negative studies

| Antiproliferative Activity | Tumor | | | | | Normal | |
|---|---|---|---|---|---|---|---|
| | A549 | Hela | PC-3 | MCF7 | H1299 | HMEC | PrEC |
| Wt | | | | | | | |
| GFP fusion | + | + | ++ | +/- | +/- | +/- | +/- |
| IRES GFP | + | + | | +/- | nd | +/- | nd |
| K41M | | | | | | | |
| GFP fusion | ++ | ++ | ++ | + | +/- | +/- | +/- |
| IRES GFP | ++ | ++ | ++ | + | nd | +/- | nd |
| D154A | | | | | | | |
| GFP fusion | ++ | nd | ++ | + | +/- | +/- | +/- |
| IRES GFP | ++ | nd | ++ | + | nd | +/- | nd |

Antisense:
| Hela | A549 | H1299 |
|---|---|---|
| + | +/- | +/- |

( + indicates antiproliferative effect in either the GFP positivity study, cell tracker or antisense studies)

FIG. 3

SAK Mutants Have a More Pronounced Antiproliferative Effect Relative to Wild Type in A549 Cells
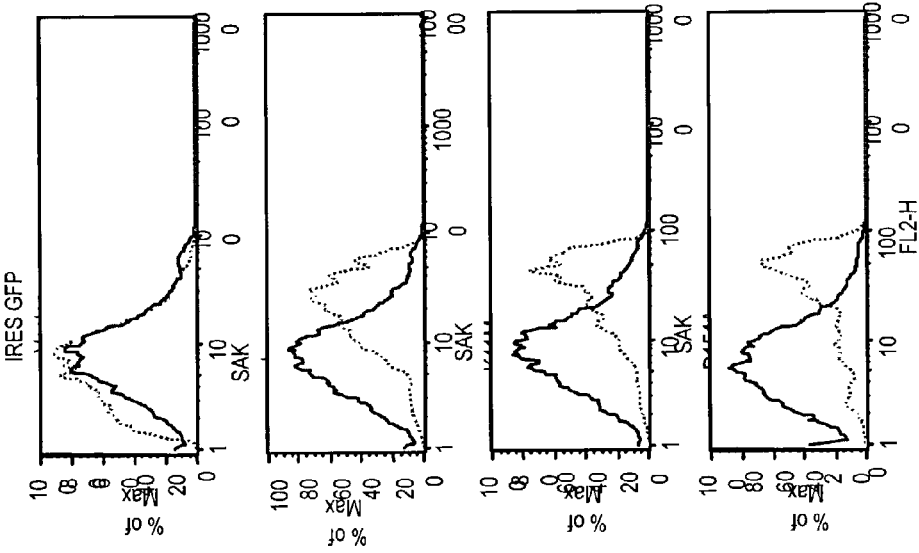
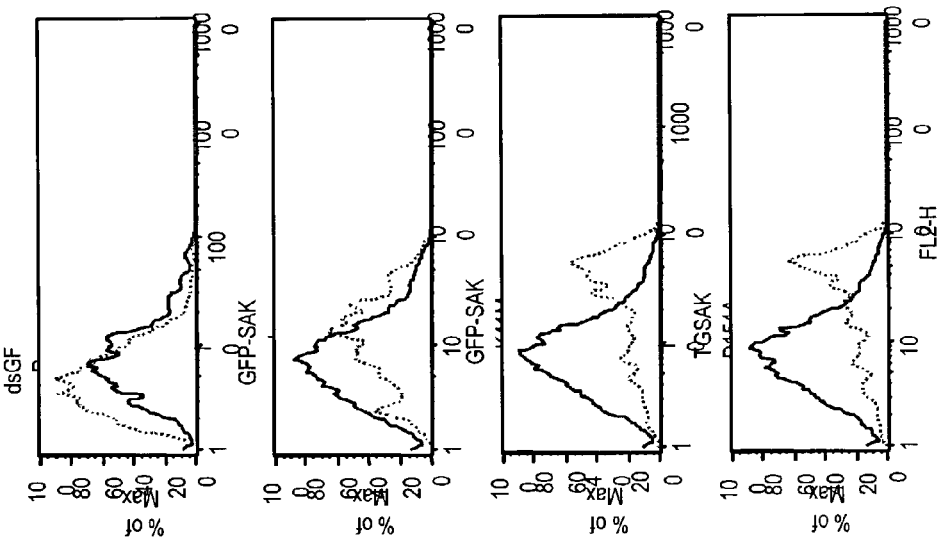
Dotted = GFP positive
Solid = GFP negative
FIG. 5

SAK Mutants Have a More Significant Antiproliferative Effect Than Wild Type in MCF7 Cells

SAK Summary

Identification
Proteomics- Chk2 interacting protein

Functional Studies

Dominant Negative Studies
- Mutant SAK has a much stronger antiproliferative phenotype than the wild type SAK in tumor cells while neither wild type or mutant SAK is antiproliferative in normal cells.
- The higher expression level of the mutant SAK relative to wild type makes it difficult to validate SAK only by the dominant negative strategy

Antisense Studies
- Preliminary studies suggests that inhibition of SAK mRNA with antisense oligos is antiproliferative in A549 and Hela cells

Literature
- Strong supporting literature shows antisense reduction of mouse SAK is antiproliferative and that the mouse SAK knockout results in increased cell cycle arrest and apoptosis

FIG. 15

Protocol for Sak Autophosphorylation Assay

Bind Sak from *E. coli* lysates to Ni-NTA agarose O/N at 4°C

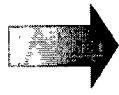

Wash Ni-NTA with lysis buffer (20 mM Hepes, pH 7.2, 0.5 M NaCl, 0.5% Tween-20, 25 mM β-glycerol phosphate, 1 mM NaF, 1 mM Na$_3$VO$_4$, 1 mM NaPyP, 10% glycerol)

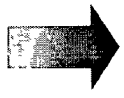

Wash Ni-NTA with kinase buffer (20 mM MOPS, pH 7.2, 25 mM β-glycerol phosphate, 5 mM EGTA, 1 mM Na$_3$VO$_4$)

Resuspend resin-bound Sak in 10 μL kinase buffer
Add 10 μL of labeling mix (20 mM MgCl$_2$, 2 mM MnCl$_2$, 0.2 mM ATP, 0.5 μCi/μL γ-$^{32}$P ATP in kinase buffer
Incubate at 30°C, 15 min.

SAK: MODULATION OF CELLULAR PROLIFERATION FOR TREATMENT OF CANCER

CROSS-REFERENCES TO RELATED APPLICATIONS

The present application claims priority to U.S. Ser. No. 60/309,632, filed Aug. 1, 2001, herein incorporated by reference in its entirety.

STATEMENT AS TO RIGHTS TO INVENTIONS MADE UNDER FEDERALLY SPONSORED RESEARCH AND DEVELOPMENT

Not applicable.

FIELD OF THE INVENTION

The present invention relates to regulation of cellular proliferation and cancer. More particularly, the present invention is directed to nucleic acids encoding SAK, which is a protein kinase involved in modulation of cellular proliferation and cell cycle regulation. The invention further relates to methods for identifying and using agents, including small molecule chemical compositions, antibodies, peptides, cyclic peptides, nucleic acids, antisense nucleic acids, RNAi, and ribozymes, that modulate cell cycle regulation and cellular proliferation via modulation of SAK; as well as to the use of expression profiles and compositions in diagnosis and therapy related to cell cycle regulation and modulation of cellular proliferation, e.g., cancer and adjuvant therapy.

BACKGROUND OF THE INVENTION

Cell cycle regulation plays a critical role in neoplastic disease, as well as disease caused by non-cancerous, pathologically proliferating cells. Normal cell proliferation is tightly regulated by the activation and deactivation of a series of proteins that constitute the cell cycle machinery. The expression and activity of components of the cell cycle can be altered during the development of a variety of human disease such as cancer, cardiovascular disease, psoriasis, where aberrant proliferation contributes to the pathology of the illness. There are genetic screens to isolate important components for cell cycle regulation using different organisms such as yeast, worms, flies, etc. However, involvement of a protein in cell cycle regulation in a model system is not always indicative of its role in cancer and other proliferative disease. Thus, there is a need to establish screening for understanding human diseases caused by disruption of cell cycle regulation. Identifying proteins, their ligands and substrates, and downstream signal transduction pathways involved in cell cycle regulation and neoplasia in humans is important for developing therapeutic regents to treat cancer and other proliferative diseases.

BRIEF SUMMARY OF THE INVENTION

The present invention therefore provides nucleic acids encoding SAK, which is a serine/threonine protein kinase involved in modulation of cellular proliferation in tumor cells. The invention therefore provides methods of screening for compounds, e.g., small organic molecules, antibodies, peptides, cyclic peptides, nucleic acids, antisense molecules, RNAi, and ribozyme, that are capable of modulating cellular proliferation and/or cell cycle regulation, e.g., either inhibiting cellular proliferation, or activating apoptosis. The compounds of the invention are also useful for enhancing sensitivity of a cell to chemotherapeutic agents, and/or to reducing toxicity of chemotherapeutic agents. Therapeutic and diagnostic methods and reagents are also provided. Modulators of SAK are therefore useful in treatment of cancer and other proliferative diseases.

In one aspect, the present invention provides a method for identifying a compound capable of interfering with binding of a SAK polypeptide or fragment thereof, the method comprising the steps of: (i) combining a SAK polypeptide or fragment thereof with a Chk2 polypeptide and the compound, wherein the SAK polypeptide or fragment thereof has kinase activity and is encoded by a nucleic acid that hybridizes under stringent conditions to a nucleic acid encoding a polypeptide having an amino acid sequence of SEQ ID NO:2; and (ii) determining the binding of the SAK polypeptide or fragment thereof to Chk2.

In one embodiment, the SAK polypeptide or fragment thereof and the Chk2 polypeptide are combined first. In another embodiment, the binding of the SAK polypeptide or fragment thereof to Chk2 is determined in vitro. In another embodiment, the SAK polypeptide or fragment thereof and the Chk2 polypeptide are expressed in a cell. In another embodiment, the cell is a yeast or a mammalian cell. In another embodiment, the SAK polypeptide or fragment thereof is fused to a heterologous polypeptide. In another embodiment, the binding of the SAK polypeptide or fragment thereof to Chk2 is determined by measuring reporter gene expression or SAK kinase activity.

In another aspect, the present invention provides a method for identifying a compound that modulates cellular proliferation, the method comprising the steps of: (i) contacting the compound with a SAK polypeptide, the polypeptide encoded by a nucleic acid that hybridizes under stringent conditions to a nucleic acid encoding a polypeptide having an amino acid sequence of SEQ ID NO:2; and (ii) determining the functional effect of the compound upon the SAK polypeptide.

In one embodiment, the functional effect is measured in vitro. In another embodiment, the polypeptide is expressed in a eukaryotic host cell or cell membrane.

In another embodiment, the functional effect is a physical effect. In another embodiment, the functional effect is determined by measuring ligand or substrate binding to the polypeptide.

In another embodiment, the functional effect is a chemical effect. In another embodiment, the functional effect is determined by measuring SAK kinase activity.

In another embodiment, the functional effect is a phenotypic effect. In another embodiment, the functional effect is determined by measuring cellular proliferation, e.g., by assaying for DNA synthesis or fluorescent marker dilution. In another embodiment, DNA synthesis is measured by $^3$H thymidine incorporation, BrdU incorporation, or Hoescht staining. In another embodiment, the fluorescent marker is selected from the group consisting of a cell tracker dye or green fluorescent protein.

In another embodiment, modulation is inhibition of cellular proliferation, e.g., cancer cell proliferation. In another embodiment, the cancer cell is a breast, prostate, colon, or lung cancer cell. In another embodiment, the cancer cell is a transformed cell line. In another embodiment, the transformed cell line is PC3, Hi299, MDA-MB-231, MCF7, A549, or HeLa. In another embodiment, the cancer cell is p53 null or mutant. In another embodiment, the cancer cell is p53 wild-type.

In another embodiment, the SAK polypeptide is recombinant. In another embodiment, the polypeptide is encoded by a nucleic acid comprising a sequence of SEQ ID NO:1.

In another embodiment, the compound is a small organic molecule, antibody, antisense molecule, RNAi molecule, peptide, or a circular peptide.

In another aspect, the present invention provides A method of modulating cellular proliferation in a subject, the method comprising the step of administering to the subject a therapeutically effective amount of a compound identified using the methods described above.

In one embodiment, the subject is a human. In another embodiment, the subject has cancer.

In another aspect, the present invention provides a method of modulating cellular proliferation in a subject, the method comprising the step of administering to the subject a therapeutically effective amount of a SAK polypeptide, the polypeptide encoded by a nucleic acid that hybridizes under stringent conditions to a nucleic acid encoding a polypeptide having an amino acid sequence of SEQ ID NO:2.

In another aspect, the present invention provides a method of modulating cellular proliferation in a subject, the method comprising the step of administering to the subject a therapeutically effective amount of a nucleic acid encoding a SAK polypeptide, wherein the nucleic acid hybridizes under stringent conditions to a nucleic acid encoding a polypeptide having an amino acid sequence of SEQ ID NO:2.

BRIEF DESCRIPTION OF THE DRAWINGS

FIG. 1 provides a nucleotide (SEQ ID NO:1) and amino acid sequence (SEQ ID NO:2) of human SAK.

FIG. 2 provides an alignment of the SAK kinase domain (SEQ ID NO:3) with other mitotic kinases (SEQ ID NOS: 4–7).

FIG. 3 provides a summary of target validation studies for SAK.

FIG. 5 provides data showing that SAK mutants have a more pronounced antiproliferative effect than wild type in A549 tumor cells.

FIG. 15 provides a summary of SAK data.

FIG. 18 shows a protocol for SAK autophosphorylation assay.

DETAILED DESCRIPTION OF THE INVENTION

Introduction

The SAK gene encodes a serine/threonine kinase, which is a member of the Polo-like family of kinases, having an N-terminal kinase domain PEST sequences, and a C-terminal polo box (pb) (see, e.g., Hudson et al., Gene 241:65–73 (2000); and Karn et al., Oncol. Rep. 4:505–510 (1997)). Members of the polo-like kinase family are thought to be involved in mitosis (see, e.g., Hudson, supra; see also Genes Dev. 12:3777–3787 (1998)). Recent studies have shown that overexpression of a SAK antisense oligonucleotide and wild type mouse SAK in CHO cells is antiproliferative (see, e.g., U.S. Pat. Nos. 5,650,501 and 5,976,893). In addition, a mouse knockout of SAK was an embryonic lethal, and embryos showed an increase in apoptosis (see, e.g., Hudson et al., Curr. Biol. 11:441–446 (2001)). However, SAK involvement in cellular transformation, tumorigenesis, and antiproliferative effects in tumor cells has never been demonstrated. Furthermore, the role of SAK in cell cycle regulation has not yet been elucidated.

Figure 4:
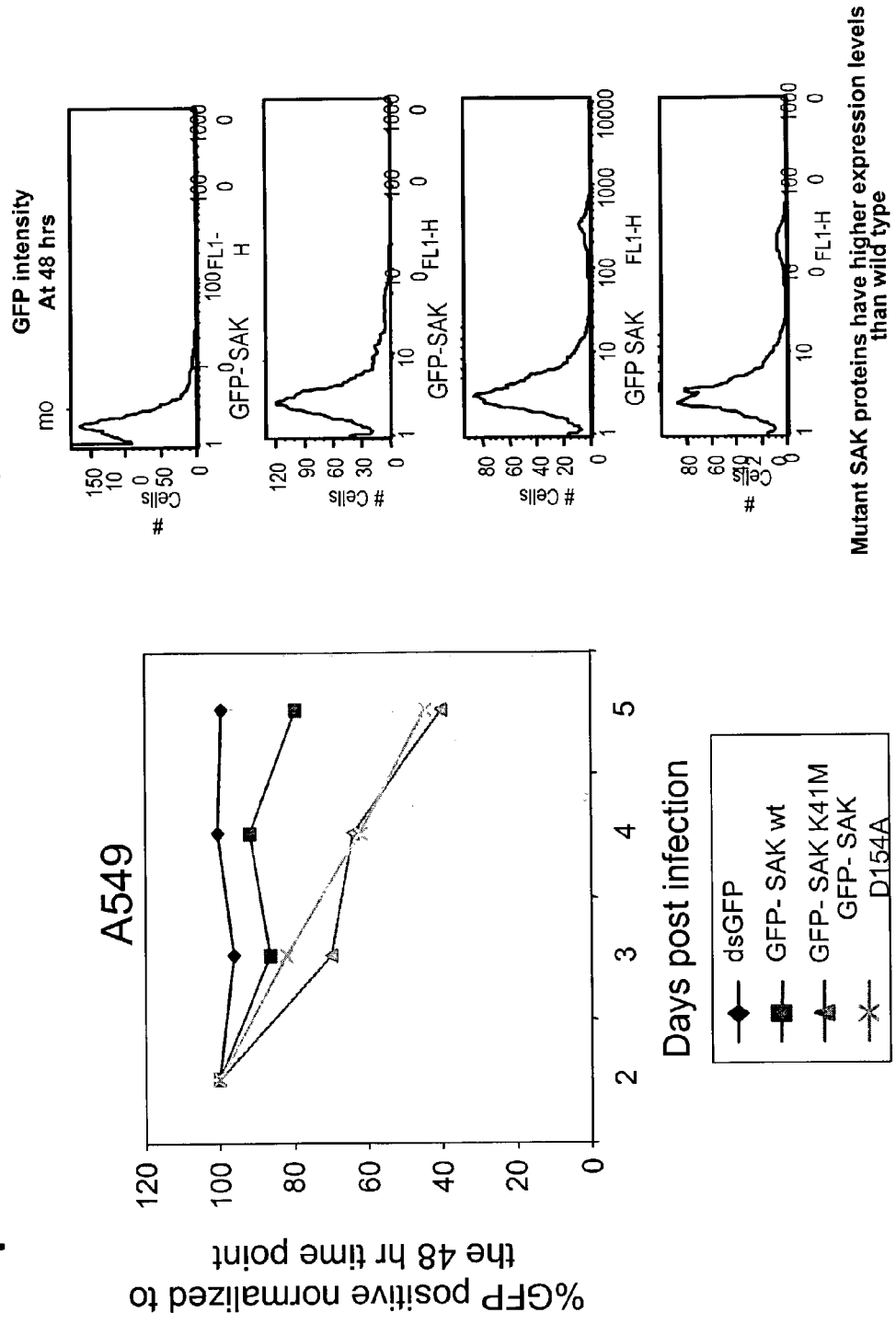
FIG. 4 provides data showing that overexpression of SAK mutants have a more pronounced antiproliferative effect than wild type in A549 tumor cells.
Figure 6:
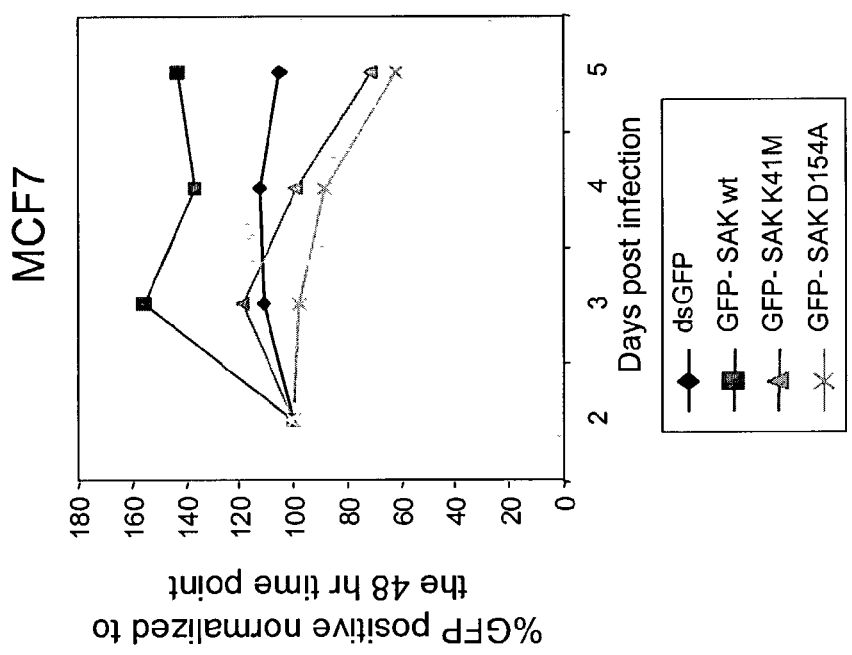
FIG. 6 provides data showing that SAK mutants have a more pronounced antiproliferative effect than wild type SAK in MCF7 cells.
Figure 7:
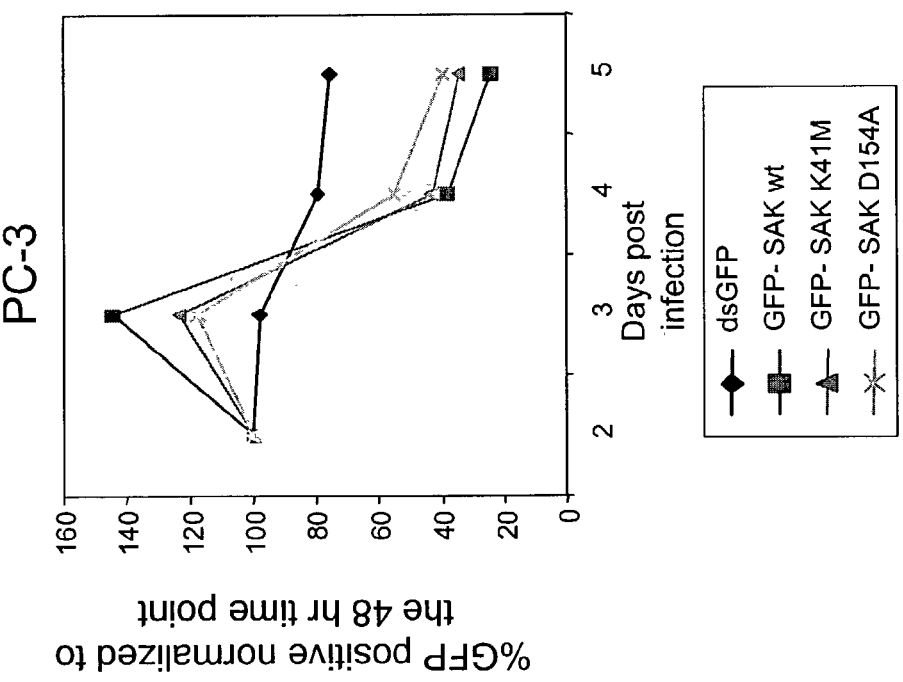
FIG. 7 provides data showing that SAK wild type and mutants have similar antiproliferative effects in PC-3 cells.
Figure 8:
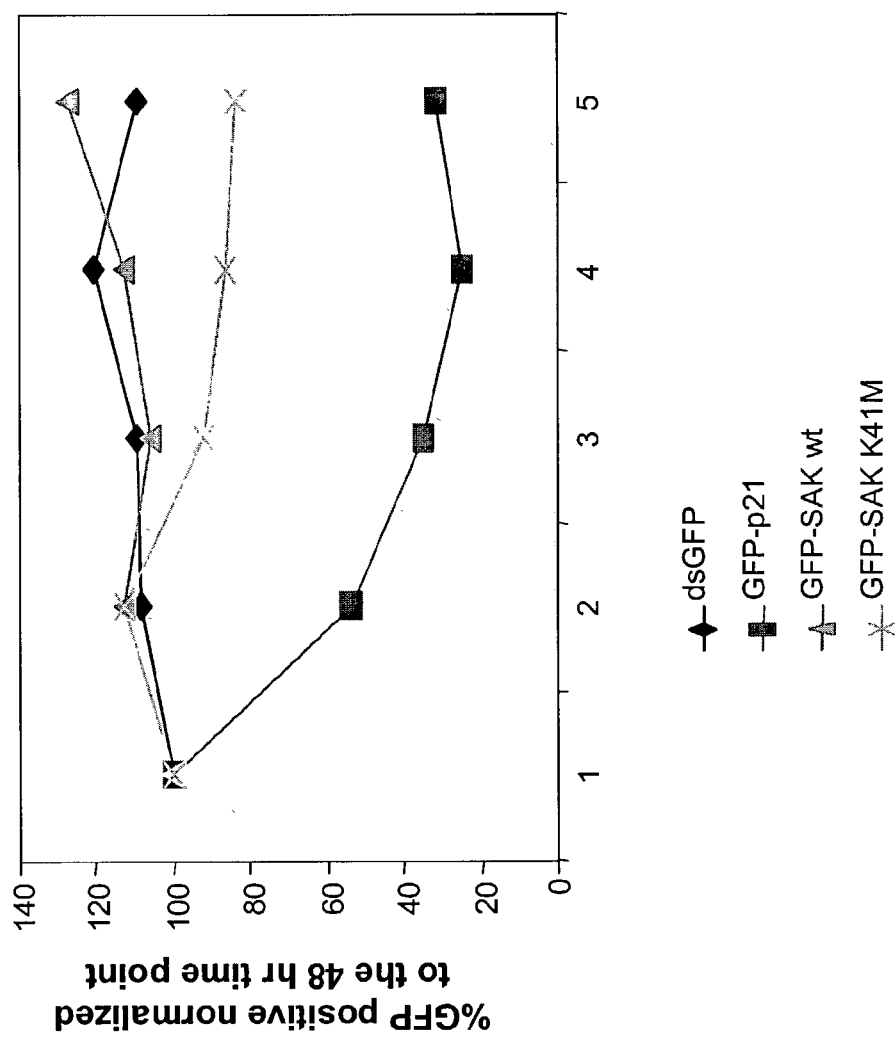
FIG. 8 provides data showing that a SAK K41M mutant has a weak antiproliferative effect in H1299 cells.
Figure 9:
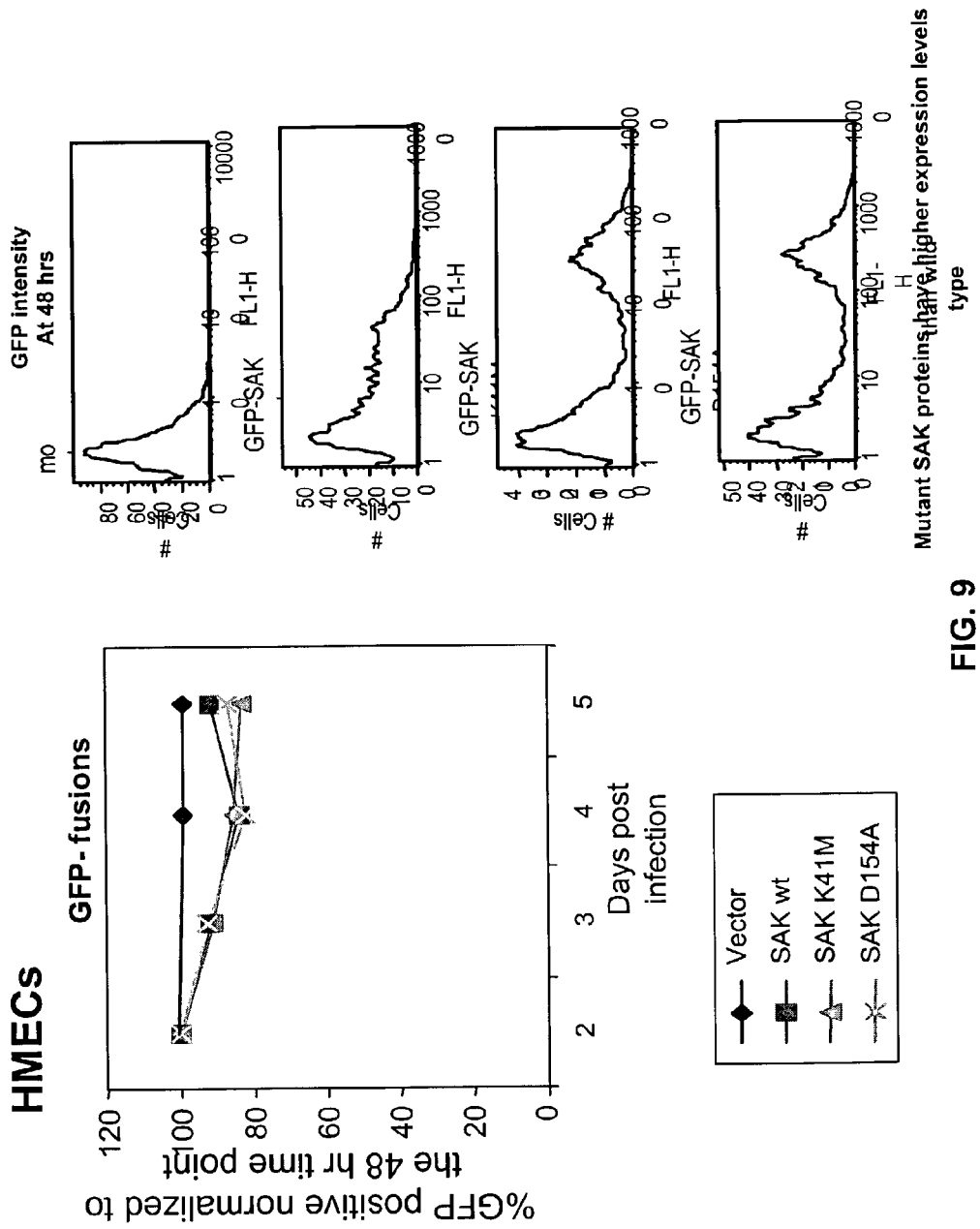
FIG. 9 provides data showing that SAK wild type and mutants have no antiproliferative effect in normal cells in GFP positivity studies.
Figure 10:
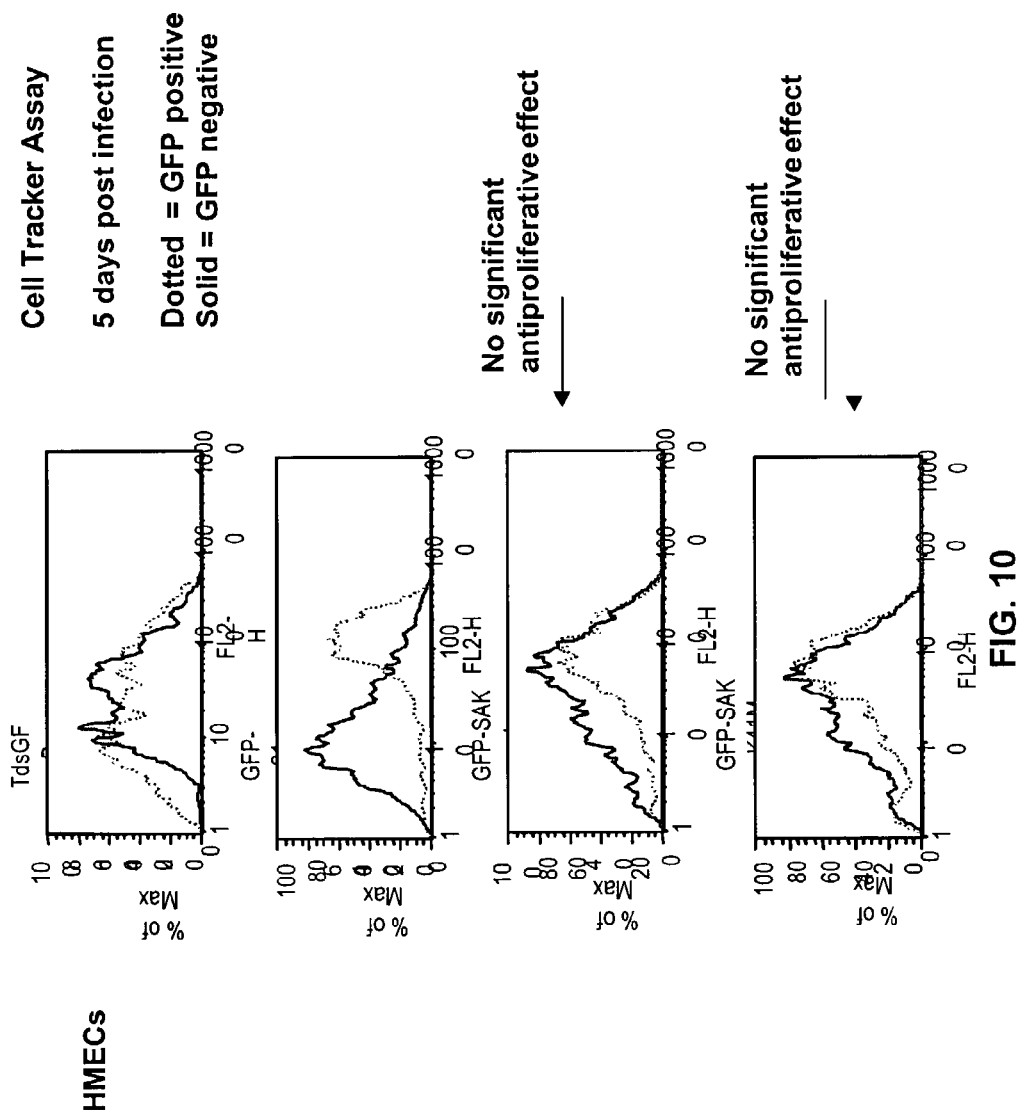
FIG. 10 provides data showing that SAK wild type and mutant proteins do not have significant antiproliferative activity in normal cells.
Figure 11:
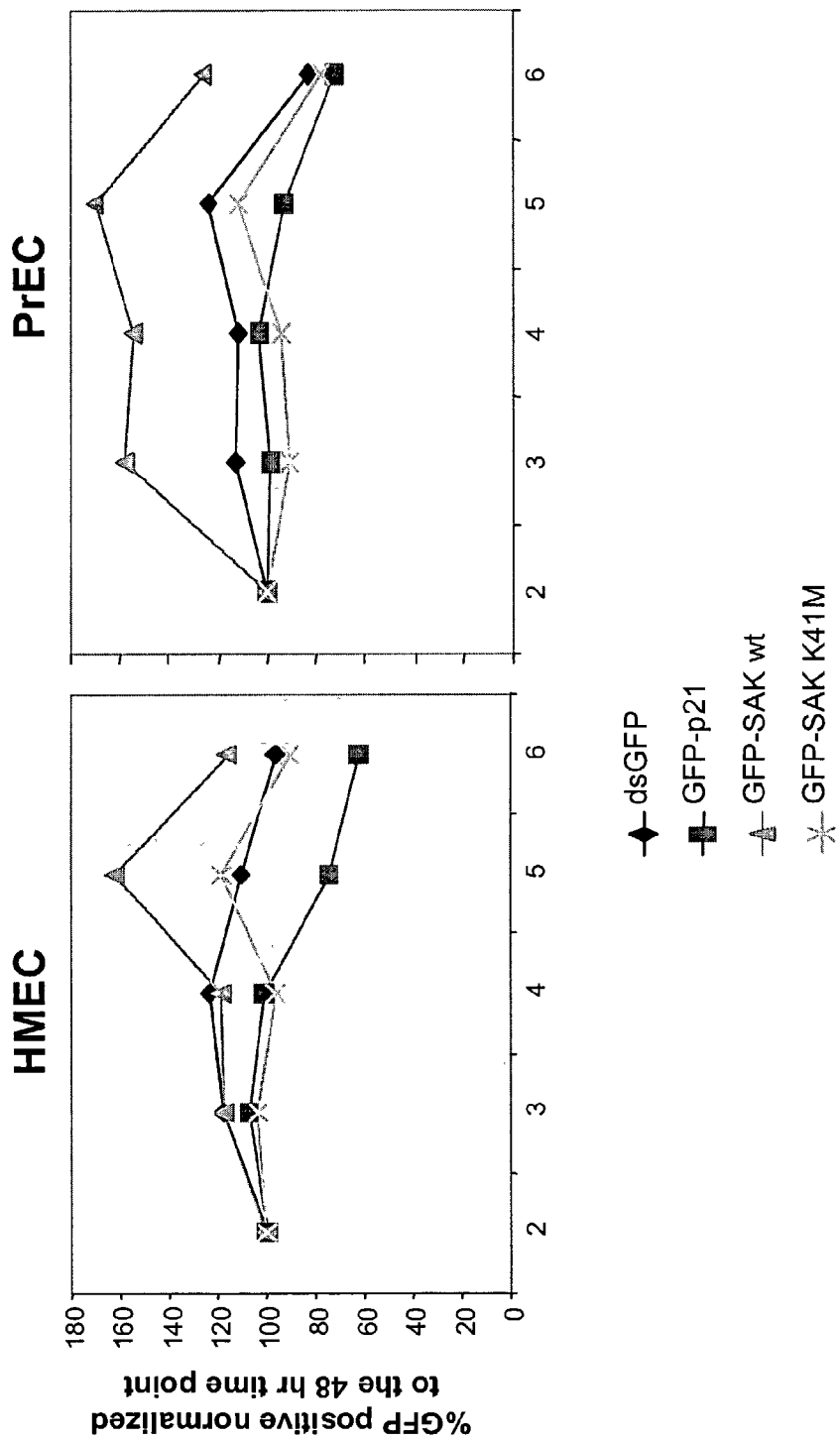
FIG. 11 provides data showing that SAK K41M mutant does not have strong antiproliferative effects in normal cells.
Figure 12:
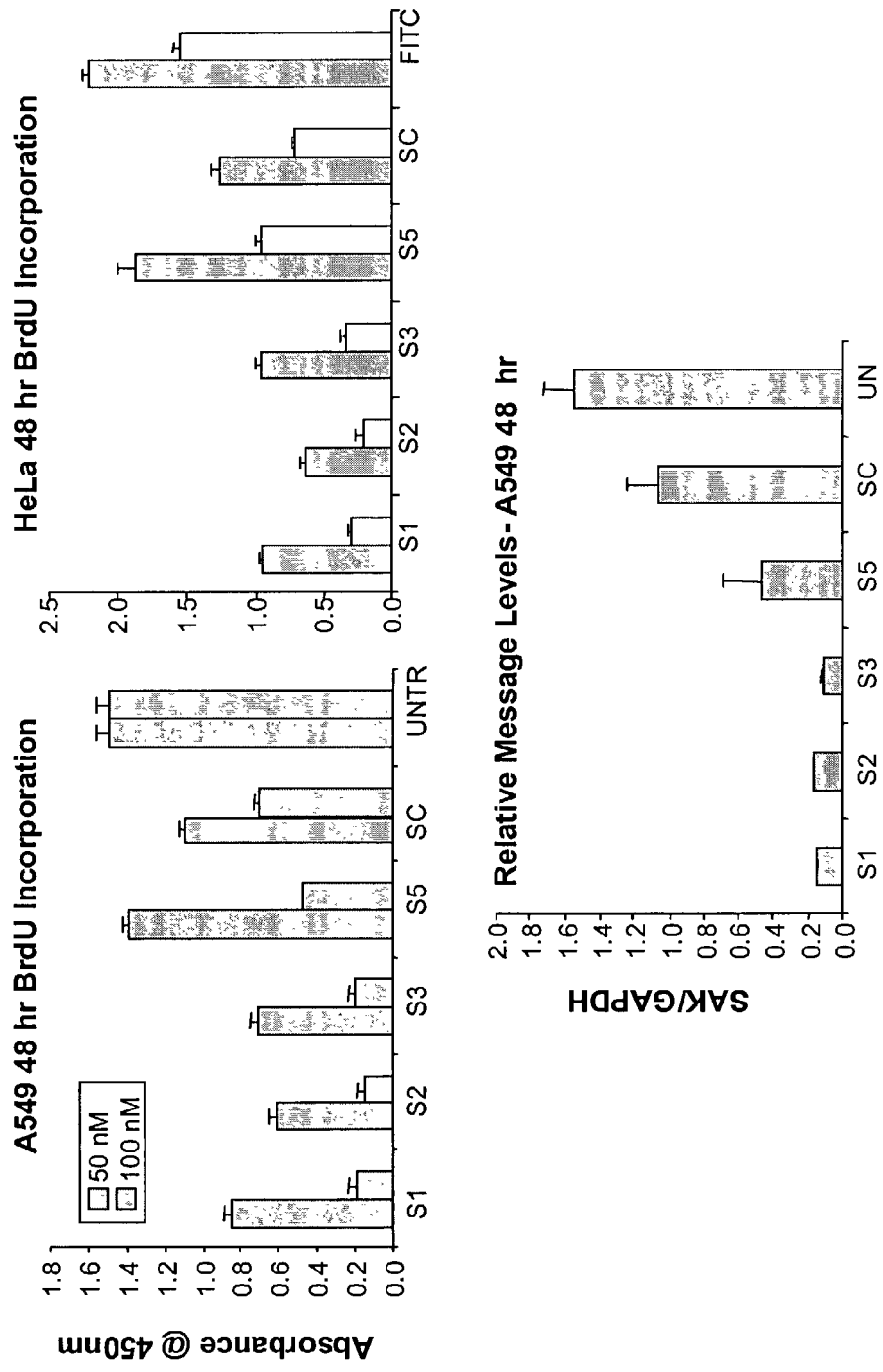
FIG. 12 provides data showing that reduction of SAK with antisense oligo transfections is antiproliferative in HeLa and A549 cancer cells.
Figure 13:
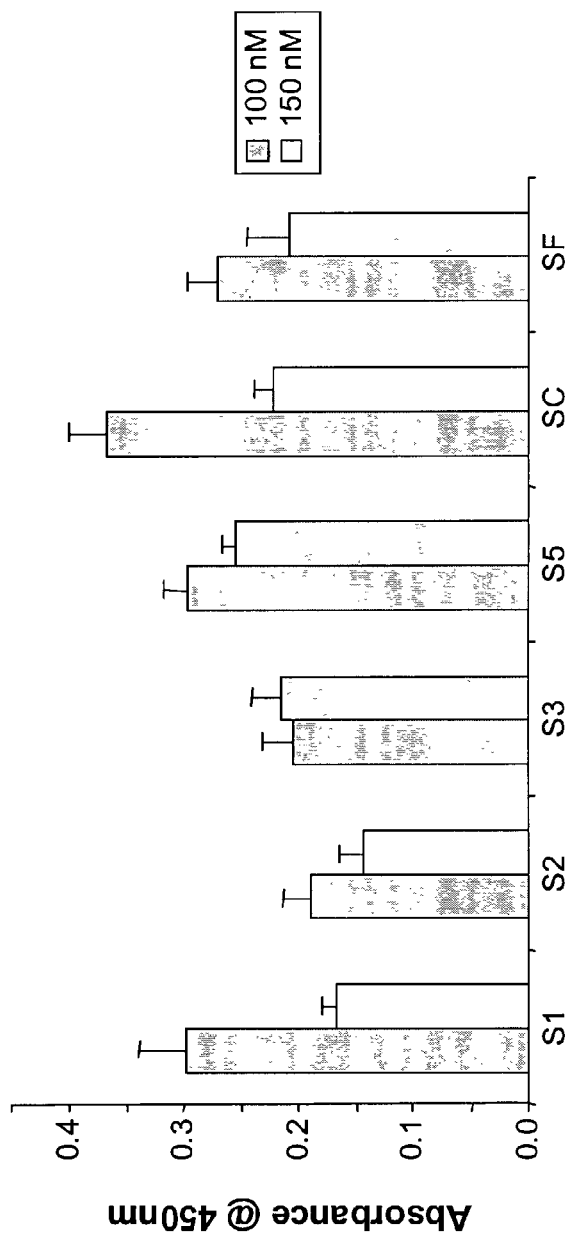
FIG. 13 provides data showing that reduction of SAK with antisense oligo transfections is weakly antiproliferative in Huvec cells.
Figure 14:
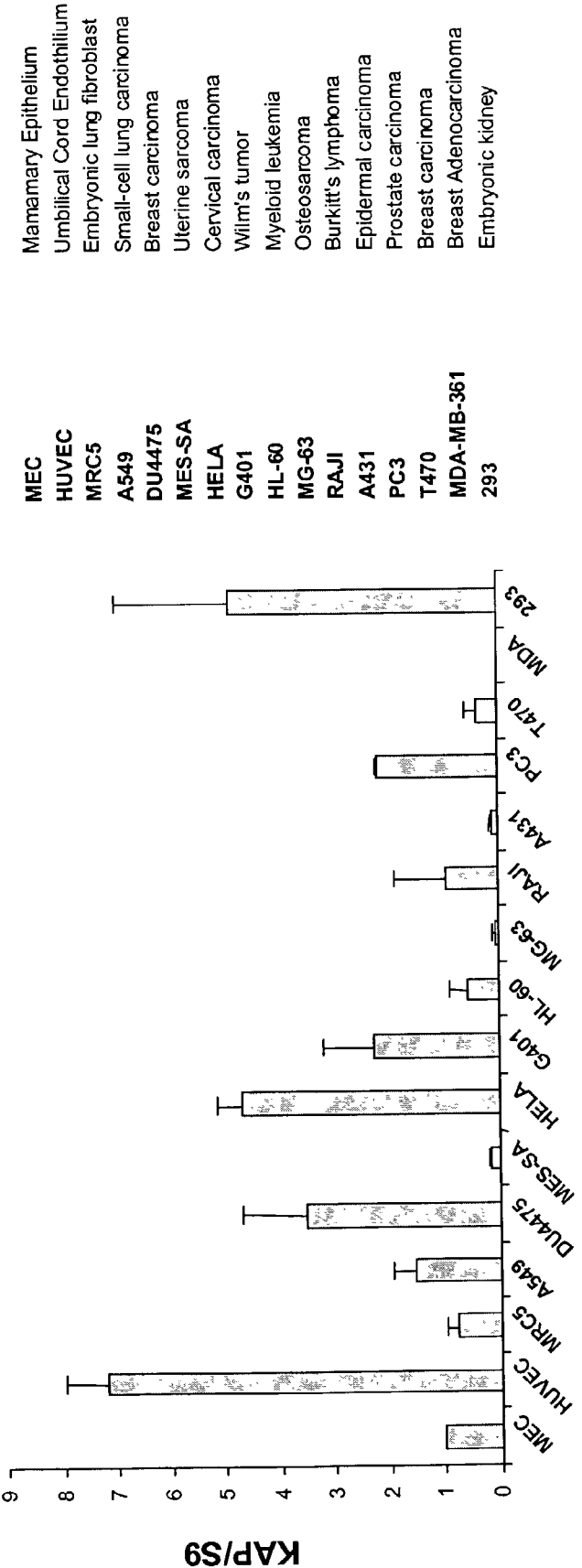
FIG. 14 provides data showing that SAK mRNA is overexpressed in some tumor cell lines.
Figure 16:
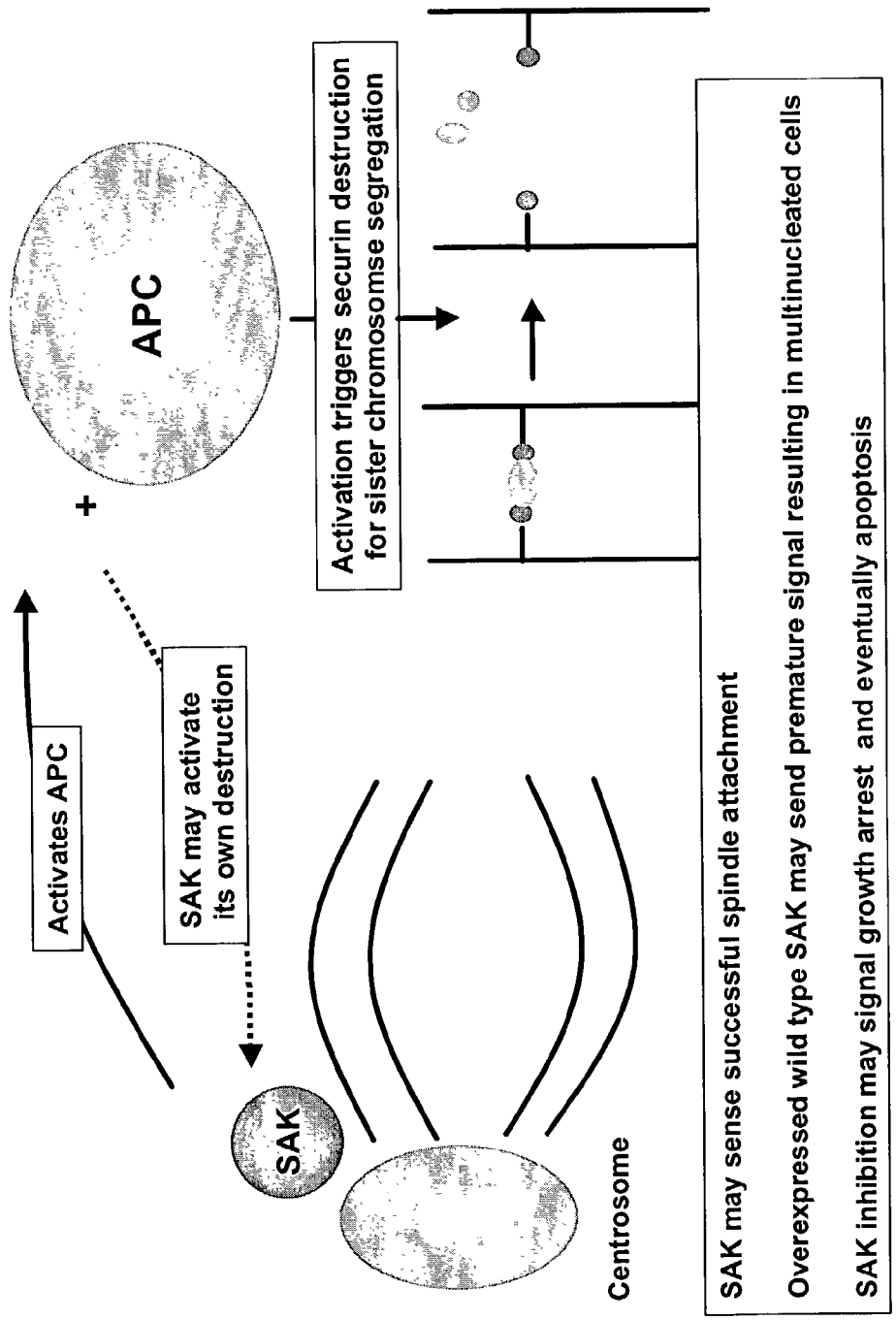
FIG. 16 provides a model for antiproliferative activity associated with SAK.

As described below, the present inventors identified human SAK in a proteomics assay, by immunoprecipitation with an anti-hChk2 antibody. Chk2 is the mammalian homolog of yeast Rad53 and is a kinase involved in cell cycle regulation (see, e.g., Matsuoka et al., Science 282:1893–1897 (1998); Blasina et al., Curr. Biol. 9:1–10 (1999); Brown et al, Proc. Nat'l Acad. Sci. USA 96:3745–3750 (1999); and Chaturvedi et al., Oncogene 18:4047–4054 (1999); see GenBank Accession number NP_009125 for a protein sequence of human Chk2 and Accession number NM_007194 for a nucleic acid sequence of human Chk2). SAK was shown to bind to Chk2 after Chk2 bound to SAK was isolated using an anti-Chk2 antibody and analyzed using mass spectroscopy (see Example 1). As shown in FIGS. 2–11, dominant negative studies with mutant SAK shown that mutant SAK has a stronger antiproliferative phenotype than wild type SAK in tumor cells, while neither wild type nor mutant SAK is antiproliferative in normal cells (using, e.g., GFP positivity and cell tracker assays). FIGS. 12–13 demonstrate that inhibition of SAK mRNA with antisense oligos is antiproliferative in A549 tumor cells and HeLa cells. Furthermore, FIG. 14 shows that SAK mRNA is overexpressed in some tumor cell lines. These functional studies, presented herein, demonstrate for the first time that inhibition of SAK will inhibit tumor cell growth.

SAK therefore represent a drug target for compounds that suppress or activate cellular proliferation in tumor cells, or cause cell cycle arrest, cause release from cell cycle arrest, activate apoptosis, increase sensitivity to chemotherapeutic (adjuvant) reagents, and decrease toxicity of chemotherapeutic reagents. Agents identified in these assays, including small organic molecules, peptides, cyclic peptides, nucleic acids, antibodies, antisense nucleic acids, RNAi, and ribozymes, that modulate cell cycle regulation and cellular proliferation via modulation of SAK, can be used to treat diseases related to cellular proliferation, such as cancer. In particular, inhibitors of SAK are useful for inhibition of cancer and tumor cell growth. SAK modulators can also be used to modulate the sensitivity of cells to chemotherapeutic agents, such as bleomycin and etoposide, and other agents known to those of skill in the art. SAK modulators can also be used to decrease toxicity of such chemotherapeutic reagents.

Figure 17:
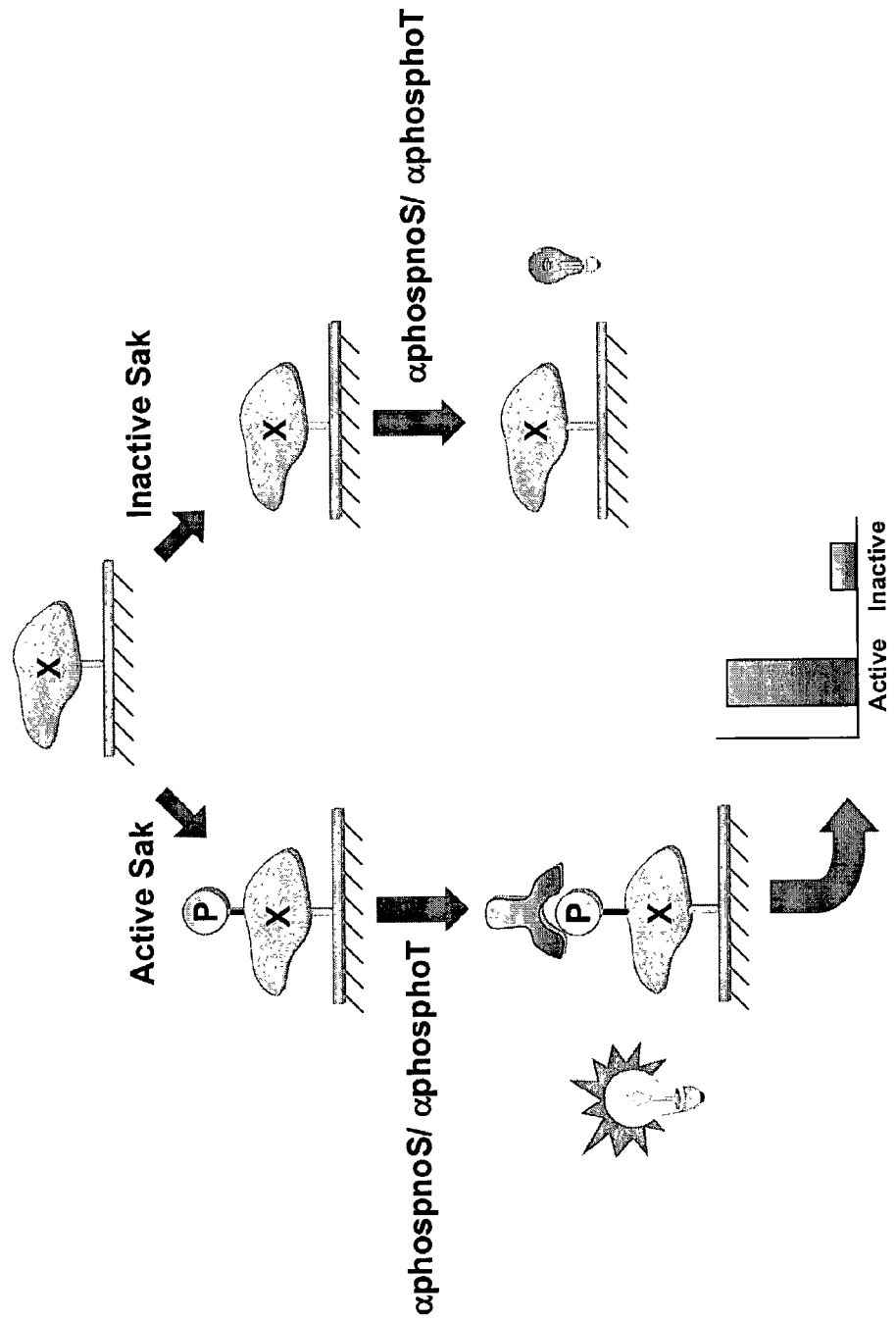
FIG. 17 shows a biochemical assay for SAK kinase activity.
Figure 19:
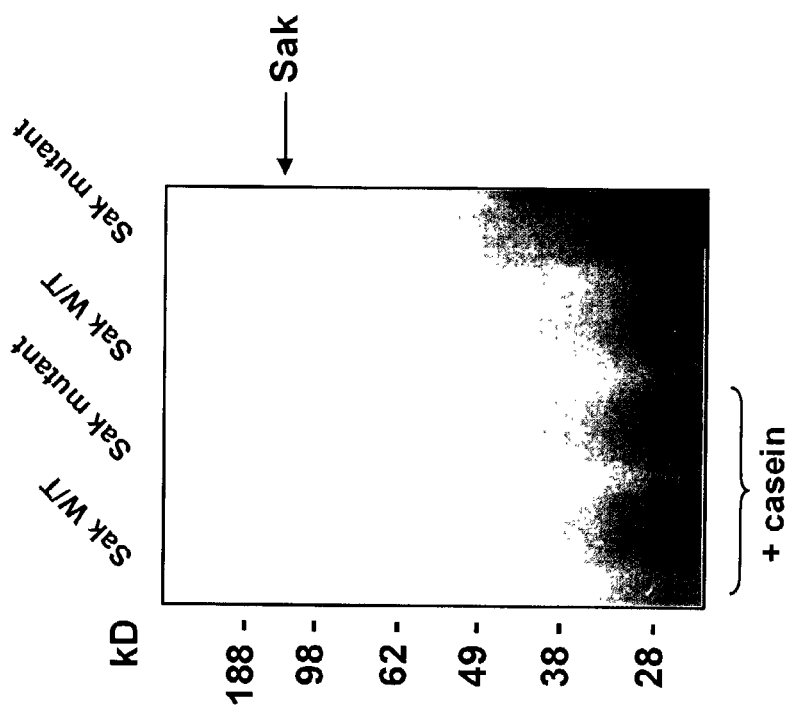
FIG. 19 shows autophosphorylation activity of SAK produced in E. coli.

In one embodiment, kinase or autophosphorylation assays using SAK can be used to identify modulators of SAK kinase activity, or to identify proteins that bind to SAK, e.g., SAK substrates. Full length wild type SAK, mutant SAK (e.g., K41M, D154A, or SAK with an internal deletion of one of the PEST sequences), or the SAK kinase domain can be used in these assays. Such assays can be performed in vitro, or can be cell-based (see, e.g., Example 2 and FIGS. 17–19). A serine/threonine kinase substrate such as MBP or a peptide having the serine/threonine kinase phosphorylation recognition site can used in such assays. For autophosphorylation assays, SAK acts both as the enzyme and the substrate. Suitable controls include kits for other kinases such as MAP kinase 1 and 2 (serine/threonine kinases), Lyn (p56) or ZAP70 (see, e.g., Isakov et al., *J. Biol. Chem.* 271:15753 (1996); Chan et al., *Cell* 71:649 (1992)).

Such modulators are useful for treating cancers, such as melanoma, breast, ovarian, lung, gastrointestinal and colon, prostate, and leukemia and lymphomas, e.g., multiple myeloma. In addition, such modulators are useful for treating noncancerous disease states caused by pathologically proliferating cells such as thyroid hyperplasia (Grave's disease), psoriasis, benign prostatic hypertrophy, neurofibromas, atherosclerosis, restenosis, and other vasoproliferative disease.

Definitions

By "disorder associated with cellular proliferation" or "disease associated with cellular proliferation" herein is meant a disease state which is marked by either an excess or a deficit of cellular proliferation or apoptosis. Such disorders associated with increased cellular proliferation include, but are not limited to, cancer and non-cancerous pathological proliferation.

The terms "SAK" or a nucleic acid encoding "SAK" refer to nucleic acids and polypeptide polymorphic variants, alleles, mutants, and interspecies homologs that: (1) have an amino acid sequence that has greater than about 60% amino acid sequence identity, 65%, 70%, 75%, 80%, 85%, 90%, preferably 91%, 92%, 93%, 94%, 95%, 96%, 97%, 98%, or 99% or greater amino acid sequence identity, preferably over a region of over a region of at least about 25, 50, 100, 200, 500, 1000, or more amino acids, to an amino acid sequence encoded by an SAK nucleic acid (for a human SAK nucleic acid sequence, see, e.g., FIG. 1, SEQ ID NO:1, or Accession number NM_014264) or amino acid sequence of an SAK protein (for a human SAK protein sequence, see, e.g., FIG. 1, SEQ ID NO:2 or Accession number NP_055079); (2) bind to antibodies, e.g., polyclonal antibodies, raised against an immunogen comprising an amino acid sequence of an SAK protein, and conservatively modified variants thereof; (3) specifically hybridize under stringent hybridization conditions to an anti-sense strand corresponding to a nucleic acid sequence encoding an SAK protein, and conservatively modified variants thereof, (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to an SAK nucleic acid or a nucleic acid encoding the kinase domain. Preferably the kinase domain has greater than 96%, 97%, 98%, or 99% amino acid identity to the human SAK kinase domain of SEQ ID NO:2. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. A SAK protein typically has kinase activity, e.g., serine/threonine kinase activity (see, e.g., FIGS. 17–19). Kinase assays can be performed according to methods known to those of skill in the art, using substrates having a serine/threonine kinase recognition site (see, e.g., MAP kinase 1 and MAP kinase 2, and ZAP-70, and commercial kits used for kinase assays). In one embodiment, a phosphorylated peptide comprising the phosphorylation recognition site is detected using an antibody that recognizes a phosphorylated serine or threonine. SAK can also be alternatively spliced (see, e.g., Hudson, supra).

The phrase "functional effects" in the context of assays for testing compounds that modulate activity of an SAK protein includes the determination of a parameter that is indirectly or directly under the influence of an SAK, e.g., an indirect, phenotypic or chemical effect, such as the ability to increase or decrease cellular proliferation, apoptosis, cell cycle arrest, or kinase activity; or e.g., a direct, physical effect such as ligand binding or inhibition of ligand binding. A functional effect therefore includes ligand binding activity, the ability of cells to proliferate, apoptosis, and enzyme activity. "Functional effects" include in vitro, in vivo, and ex vivo activities.

By "determining the functional effect" is meant assaying for a compound that increases or decreases a parameter that is indirectly or directly under the influence of an SAK protein, e.g., measuring physical and chemical or phenotypic effects. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g. binding to antibodies; measuring changes in ligand or substrate binding activity; measuring cellular proliferation; measuring apoptosis; measuring cell surface marker expression; measurement of changes in protein levels for SAK-associated sequences; measurement of RNA stability; phosphorylation or dephosphorylation; kinase activity; identification of downstream or reporter gene expression (CAT, luciferase, β-gal, GFP and the like), e.g., via chemiluminescence, fluorescence, colorimetric reactions, antibody binding, and inducible markers.

"Inhibitors", "activators", and "modulators" of SAK polynucleotide and polypeptide sequences are used to refer to activating, inhibitory, or modulating molecules identified using in vitro and in vivo assays of SAK polynucleotide and polypeptide sequences. Inhibitors are compounds that, e.g., bind to, partially or totally block activity, decrease, prevent, delay activation, inactivate, desensitize, or down regulate the activity or expression of SAK proteins, e.g., antagonists. "Activators" are compounds that increase, open, activate, facilitate, enhance activation, sensitize, agonize, or up regulate SAK protein activity, e.g., agonists. Inhibitors, activators, or modulators also include genetically modified versions of SAK proteins, e.g., versions with altered activity, as well as naturally occurring and synthetic ligands, antagonists, agonists, antibodies, peptides, cyclic peptides, nucleic acids, antisense molecules, ribozymes, small chemical molecules and the like. Such assays for inhibitors and activators include, e.g., expressing SAK protein in vitro, in cells, or cell membranes, applying putative modulator compounds, and then determining the functional effects on activity, as described above.

Samples or assays comprising SAK proteins that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of SAK is achieved when the activity value relative to the control is about 80%, preferably 50%, more preferably 25–0%. Activation of SAK is achieved when the activity value relative to the control (untreated with activators) is 110%, more preferably 150%, more preferably 200–500% (i.e., two to five fold higher relative to the control), more preferably 1000–3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid, fatty acid, polynucleotide, oligonucleotide, etc., to be tested for the capacity to directly or indirectly modulation tumor cell proliferation. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence SEQ ID NO:1 or amino acid sequence SEQ ID NO:2), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., enzymatic domains, extracellular domains, transmembrane domains, pore domains, and cytoplasmic tail domains. Domains are portions of a polypeptide that form a compact unit of the polypeptide and are typically 15 to 350 amino acids long. Exemplary domains include domains with enzymatic activity, e.g., a kinase domain. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.–95° C. for 30 sec–2 min., an annealing phase lasting 30 sec.–2 min., and an extension phase of about 72° C. for 1–2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$–$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990))

For preparation of antibodies, e.g., recombinant, monoclonal, or polyclonal antibodies, many technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016; Marks et al., *Bio/Technology* 10:779–783 (1992); Lonberg et al., *Nature* 368:856–859 (1994); Morrison, *Nature* 368:812–13 (1994); Fishwild et al., *Nature Biotechnology* 14:845–51 (1996); Neuberger, *Nature Biotechnology* 14:826 (1996); and Lonberg & Huszar, *Intern. Rev. Immunol.* 13:65–93 (1995)). Alternatively, phage display technology can be used to identify antibodies and heteromeric Fab fragments that specifically bind to selected antigens (see, e.g., McCafferty et al., *Nature* 348:552–554 (1990); Marks et al., *Biotechnology* 10:779–783 (1992)). Antibodies can also be made bispecific, i.e., able to recognize two different antigens (see, e.g., WO 93/08829, Traunecker et al., *EMBO J.* 10:3655–3659 (1991); and Suresh et al., *Methods in Enzymology* 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature* 321:522–525 (1986); Riechmann et al., *Nature* 332: 323–327 (1988); Verhoeyen et al., *Science* 239:1534–1536 (1988) and Presta, *Curr. Op. Struct. Biol.* 2:593–596 (1992)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a SAK protein, polymorphic variants, alleles, orthologs, and conservatively modified variants, or splice variants, or portions thereof, can be selected to obtain only those polyclonal antibodies that are specifically immunoreactive with SAK proteins and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

By "therapeutically effective dose" herein is meant a dose that produces effects for which it is administered. The exact dose will depend on the purpose of the treatment, and will be ascertainable by one skilled in the art using known techniques (see, e.g., Lieberman, *Pharmaceutical Dosage Forms* (vols. 1–3, 1992); Lloyd, *The Art, Science and Technology of Pharmaceutical Compounding* (1999); and Pickar, *Dosage Calculations* (1999)).

Assays for Proteins that Modulation Cellular Proliferation

High throughput functional genomics assays can be used to identify modulators of cellular proliferation. Such assays can monitor changes in cell surface marker expression, proliferation and differentiation, and apoptosis, using either cell lines or primary cells. Typically, the cells are contacted with a cDNA or a random peptide library (encoded by nucleic acids). In one embodiment, the peptides are cyclic or circular. The cDNA library can comprise sense, antisense, full length, and truncated cDNAs. The peptide library is encoded by nucleic acids. The effect of the cDNA or peptide library on the phenotype of cellular proliferation is then monitored, using an assay as described above. The effect of the cDNA or peptide can be validated and distinguished from somatic mutations, using, e.g., regulatable expression of the nucleic acid such as expression from a tetracycline promoter. cDNAs and nucleic acids encoding peptides can be rescued using techniques known to those of skill in the art, e.g., using a sequence tag.

Proteins interacting with the peptide or with the protein encoded by the cDNA (e.g., SAK) can be isolated using a yeast two-hybrid system, mammalian two hybrid system, immunoprecipitation or affinity chromatography of complexed proteins followed by mass spectrometry, or phage display screen, etc. Targets so identified can be further used as bait in these assays to identify additional members of the cellular proliferation pathway, which members are also targets for drug development (see, e.g., Fields et al., *Nature* 340:245 (1989); Vasavada et al., *Proc. Nat'l. Acad. Sci. USA* 88:10686 (1991); Fearon et al., *Proc. Nat'l. Acad. Sci. USA* 89:7958 (1992); Dang et al., *Mol. Cell. Biol.* 11:954 (1991);

Chien et al., *Proc. Nat'l. Acad. Sci. USA* 9578 (1991); and U.S. Pat. Nos. 5,283,173, 5,667,973, 5,468,614, 5,525,490, and 5,637,463).

Suitable cell lines include A549, HeLa, Colo205, H1299, MCF7, MDA-MB-231, PC3, HMEC, PrEC. Cell surface markers can be assayed using fluorescently labeled antibodies and FACS. Cell proliferation can be measured using $^3$H-thymidine incorporation, cell count by dye inclusion, MTT assay, BrdU incorporation, Cell Tracker assay. Apoptosis can be measured using dye inclusion, or by assaying for DNA laddering, increases in intracellular calcium, or caspare activation. Growth factor production can be measured using an immunoassay such as ELISA.

cDNA libraries are made from any suitable source. Libraries encoding random peptides are made according to techniques well known to those of skill in the art (see, e.g., U.S. Pat. Nos. 6,153,380, 6,114,111, and 6,180,343). Any suitable vector can be used for the cDNA and peptide libraries, including, e.g., retroviral vectors.

Isolation of Nucleic Acids Encoding SAK Family Members

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

SAK nucleic acids, polymorphic variants, orthologs, and alleles that are substantially identical to an amino acid sequence encoded by SEQ ID NO:2 can be isolated using SAK nucleic acid probes and oligonucleotides under stringent hybridization conditions, by screening libraries. Alternatively, expression libraries can be used to clone SAK protein, polymorphic variants, orthologs, and alleles by detecting expressed homologs immunologically with antisera or purified antibodies made against human SAK or portions thereof.

To make a cDNA library, one should choose a source that is rich in SAK RNA. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating SAK nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human SAK directly from mRNA, from cDNA, from genomic libraries or cDNA libraries. Degenerate oligonucleotides can be designed to amplify SAK homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of SAK encoding mRNA in physiological samples, for nucleic acid sequencing, or for other purposes. Genes amplified by the PCR reaction can be purified from agarose gels and cloned into an appropriate vector.

Gene expression of SAK can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology, e.g., and the like.

Nucleic acids encoding SAK protein can be used with high density oligonucleotide array technology (e.g., GeneChip™) to identify SAK protein, orthologs, alleles, conservatively modified variants, and polymorphic variants in this invention. In the case where the homologs being identified are linked to modulation of cellular proliferation, they can be used with GeneChip™ as a diagnostic tool in detecting the disease in a biological sample, see, e.g., Gunthand et al., *AIDS Res. Hum. Retroviruses* 14:869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

The gene for SAK is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding SAK, one typically subclones SAK into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the SAK protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the SAK encoding nucleic acid in host cells. A typical expression cassette thus contains a promoter operably linked to the nucleic acid sequence encoding SAK and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *PNAS* 89:5547 (1992); Oligino et al., *Gene Ther.* 5:491–496 (1998); Wang et al., *Gene Ther.* 4:432–441 (1997); Neering et al., *Blood* 88:1147–1155 (1996); and Rendahl et al., *Nat. Biotechnol.* 16:757–761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a SAK encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of SAK protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing SAK.

After the expression vector is introduced into the cells, the transfected cells are cultured under conditions favoring expression of SAK, which is recovered from the culture using standard techniques identified below.

Purification of SAK Polypeptides

Either naturally occurring or recombinant SAK can be purified for use in functional assays. Naturally occurring SAK can be purified, e.g., from human tissue. Recombinant SAK can be purified from any suitable expression system.

The SAK protein may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant SAK protein is being purified. For example, proteins having established molecular adhesion properties can be reversible fused to the SAK protein. With the appropriate ligand or substrate, e.g., antiphospho S/T antibodies or anti-SAK antibodies, SAK protein can be selectively adsorbed to a purification column and then freed from the column in a relatively pure form. The fused protein is then removed by enzymatic activity. Finally, SAK protein could be purified using immunoaffinity columns. Recombinant SAK protein can be purified from any suitable source, include yeast, insect, bacterial, and mammalian cells.

A. Purification of SAK from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of SAK protein inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM MgCl$_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human SAK proteins are separated from other bacterial proteins by standard separation techniques, e.g., with Ni-NTA agarose resin.

Alternatively, it is possible to purify SAK protein from bacteria periplasm. After lysis of the bacteria, when the SAK protein exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO$_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifing SAK Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the SAK proteins can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The SAK proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of SAK Protein

A. Assays

Modulation of an SAK protein, and corresponding modulation of cellular, e.g., tumor cell, proliferation, can be assessed using a variety of in vitro and in vivo assays, including cell-based models. Such assays can be used to test for inhibitors and activators of SAK protein, and, consequently, inhibitors and activators of cellular proliferation, including modulators of chemotherapeutic sensitivity and toxicity. Such modulators of SAK protein are useful for treating disorders related to pathological cell proliferation, e.g., cancer. Modulators of SAK protein are tested using either recombinant or naturally occurring SAK, preferably human SAK.

Preferably, the SAK protein will have the sequence as encoded by SEQ ID NO:2 or a conservatively modified variant thereof. Alternatively, the SAK protein of the assay will be derived from a eukaryote and include an amino acid subsequence having substantial amino acid sequence identity to SEQ ID NO:2. Generally, the amino acid sequence identity will be at least 60%, preferably at least 65%, 70%, 75%, 80%, 85%, or 90%, most preferably at least 95%.

Measurement of cellular proliferation modulation with SAK protein or a cell expressing SAK protein, either recombinant or naturally occurring, can be performed using a variety of assays, in vitro, in vivo, and ex vivo, as described herein. A suitable physical, chemical or phenotypic change that affects activity, e.g., enzymatic activity such as kinase activity, cell proliferation, or ligand binding (e.g., Chk2) can be used to assess the influence of a test compound on the polypeptide of this invention. When the functional effects are determined using intact cells or animals, one can also measure a variety of effects, such as, ligand binding, kinase activity, transcriptional changes to both known and uncharacterized genetic markers (e.g., northern blots), changes in cell metabolism, changes related to cellular proliferation, cell surface marker expression, DNA synthesis, marker and dye dilution assays (e.g., GFP and cell tracker assays), contact inhibition, tumor growth in nude mice, etc.

In vitro Assays

Assays to identify compounds with SAK modulating activity can be performed in vitro. Such assays can used full length SAK protein or a variant thereof (see, e.g., SEQ ID NO:2), or a mutant thereof, e.g., K41M or D154A, or a fragment of an SAK protein, such as a kinase domain. Purified recombinant or naturally occurring SAK protein can be used in the in vitro methods of the invention. In addition to purified SAK protein, the recombinant or naturally occurring SAK protein can be part of a cellular lysate or a cell membrane. As described below, the binding assay can be either solid state or soluble. Preferably, the protein or membrane is bound to a solid support, either covalently or non-covalently. Often, the in vitro assays of the invention are substrate or ligand binding or affinity assays, either non-competitive or competitive (with a ligand such as Chk2 or a substrate having a serine/threonine phosphorylation site). Other in vitro assays include measuring changes in spectroscopic (e.g., fluorescence, absorbance, refractive index), hydrodynamic (e.g., shape), chromatographic, or solubility properties for the protein. Other in vitro assays include enzymatic activity assays, such as phosphorylation or autophosphorylation assays (see, e.g., FIGS. 17–19).

In one embodiment, a high throughput binding assay is performed in which the SAK protein or a fragment thereof is contacted with a potential modulator and incubated for a suitable amount of time. In one embodiment, the potential modulator is bound to a solid support, and the SAK protein is added. In another embodiment, the SAK protein is bound to a solid support. A wide variety of modulators can be used, as described below, including small organic molecules, peptides, antibodies, and SAK ligand analogs. A wide variety of assays can be used to identify SAK-modulator binding, including labeled protein-protein binding assays, electrophoretic mobility shifts, immunoassays, enzymatic assays such as kinase assays, and the like. In some cases, the binding of the candidate modulator is determined through the use of competitive binding assays, where interference with binding of a known ligand or substrate is measured in the presence of a potential modulator. Either the modulator or the known ligand or substrate is bound first, and then the competitor is added. After the SAK protein is washed, interference with binding, either of the potential modulator or of the known ligand or substrate, is determined. Often, either the potential modulator or the known ligand or substrate is labeled.

Cell-based in vitro Assays

In another embodiment, SAK protein is expressed in a cell, and functional, e.g., physical and chemical or phenotypic, changes are assayed to identify SAK and modulators of cellular proliferation, e.g., tumor cell proliferation. Cells expressing SAK proteins can also be used in binding assays and enzymatic assays. Any suitable functional effect can be measured, as described herein. For example, cellular morphology (e.g., cell volume, nuclear volume, cell perimeter, and nuclear perimeter), ligand binding, kinase activity, apoptosis, cell surface marker expression, cellular proliferation, GFP positivity and dye dilution assays (e.g., cell tracker assays with dyes that bind to cell membranes), DNA synthesis assays (e.g., $^3$H-thymidine and fluorescent DNA-binding dyes such as BrdU or Hoescht dye with FACS analysis), are all suitable assays to identify potential modulators using a cell based system. Suitable cells for such cell based assays include both primary cancer or tumor cells and cell lines, as described herein, e.g., A549 (lung), MCF7 (breast, p53 wild-type), H1299 (lung, p53 null), Hela (cervical), PC3 (prostate, p53 mutant), MDA-MB231 (breast, p53 wild-type). Cancer cell lines can be p53 mutant, p53 null, or express wild type p53. The SAK protein can be naturally occurring or recombinant. Also, fragments of SAK or chimeric SAK proteins with kinase activity can be used in cell based assays.

Cellular SAK polypeptide levels can be determined by measuring the level of protein or mRNA. The level of SAK protein or proteins related to SAK are measured using immunoassays such as western blotting, ELISA and the like with an antibody that selectively binds to the SAK polypeptide or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, SAK expression can be measured using a reporter gene system. Such a system can be devised using an SAK protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961–964 (1997)). The reporter construct is typically transfected into a cell. After treatment with a potential modulator, the amount of reporter gene transcription, translation, or activity is measured according to standard techniques known to those of skill in the art.

Animal Models

Animal models of cellular proliferation also find use in screening for modulators of cellular proliferation. Similarly, transgenic animal technology including gene knockout technology, for example as a result of homologous recombination with an appropriate gene targeting vector, or gene overexpression, will result in the absence or increased expression of the SAK protein. The same technology can also be applied to make knock-out cells. When desired, tissue-specific expression or knockout of the SAK protein may be necessary. Transgenic animals generated by such methods find use as animal models of cellular proliferation and are additionally useful in screening for modulators of cellular proliferation.

Knock-out cells and transgenic mice can be made by insertion of a marker gene or other heterologous gene into an endogenous SAK gene site in the mouse genome via homologous recombination. Such mice can also be made by substituting an endogenous SAK with a mutated version of the SAK gene, or by mutating an endogenous SAK, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

Exemplary Assays

Kinase Activity Assays—in vitro or Cell Based

In one embodiment, kinase or autophosphorylation assays using SAK can be used to identify modulators of SAK kinase activity, or to identify proteins that bind to SAK, e.g., SAK substrates. Full length wild type SAK, mutant SAK (e.g., K41M or D154A), or the SAK kinase domain can be used in these assays. Such assays can be performed in vitro, using recombinant SAK or cellular lysates comprising endogenous or recombinant SAK, or can be cell-based (see, e.g., Example 2 and FIGS. 17–19). A serine/threonine kinase substrate such as MBP or a peptide having the serine/threonine kinase phosphorylation recognition site can used in such assays. For autophosphorylation assays, SAK acts both as the enzyme and the substrate. Suitable controls include kits for other kinases such as MAP kinase 1 and 2 (serine/threonine kinases) or ZAP70 (see, e.g., Isakov et al., *J. Biol. Chem.* 271:15753 (1996); Chan et al., *Cell* 71:649 (1992)). In one embodiment, an anti-phospo S/T antibody conjugated to HRP is used with a to detect phosphorylation of a generic substrate by SAK, and detected after incubation with a chemiluminescent HRP substrate.

Soft Agar Growth or Colony Formation in Suspension

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Soft agar growth or colony formation in suspension assays can be used to identify SAK modulators. Typically, transformed host cells (e.g., cells that grow on soft agar) are used in this assay. For example, RKO or HCT116 cell lines can be used. Techniques for soft agar growth or colony formation in suspension assays are described in Freshney, *Culture of Animal Cells a Manual of Basic Technique*, $3^{rd}$ ed., Wiley-Liss, New York (1994), herein incorporated by reference. See also, the methods section of Garkavtsev et al. (1996), supra, herein incorporated by reference.

Contact Inhibition and Density Limitation of Growth

Normal cells typically grow in a flat and organized pattern in a petri dish until they touch other cells. When the cells touch one another, they are contact inhibited and stop growing. When cells are transformed, however, the cells are not contact inhibited and continue to grow to high densities in disorganized foci. Thus, the transformed cells grow to a higher saturation density than normal cells. This can be detected morphologically by the formation of a disoriented monolayer of cells or rounded cells in foci within the regular pattern of normal surrounding cells. Alternatively, labeling index with [$^3$H]-thymidine at saturation density can be used to measure density limitation of growth. See Freshney (1994), supra. The transformed cells, when contacted with cellular proliferation modulators, regenerate a normal phenotype and become contact inhibited and would grow to a lower density.

Contact inhibition and density limitation of growth assays can be used to identify SAK modulators which are capable of inhibiting abnormal proliferation and transformation in host cells. Typically, transformed host cells (e.g., cells that are not contact inhibited) are used in this assay. For example, RKO or HCT116 cell lines can be used. In this assay, labeling index with [$^3$H]-thymidine at saturation density is a preferred method of measuring density limitation of growth. Transformed host cells are contacted with a potential SAK modulator and are grown for 24 hours at saturation density in non-limiting medium conditions. The percentage of cells labeling with [$^3$H]-thymidine is determined autoradiographically. See, Freshney (1994), supra. The host cells contacted with a SAK modulator would give arise to a lower labeling index compared to control (e.g., transformed host cells transfected with a vector lacking an insert).

Growth Factor or Serum Dependence

Growth factor or serum dependence can be used as an assay to identify SAK modulators. Transformed cells have a lower serum dependence than their normal counterparts (see, e.g., Temin, *J. Natl. Cancer Insti.* 37:167–175 (1966); Eagle et al., *J. Exp. Med.* 131:836–879 (1970)); Freshney, supra. This is in part due to release of various growth factors by the transformed cells. When transformed cells are contacted with a SAK modulator, the cells would reacquire serum dependence and would release growth factors at a lower level.

Tumor Specific Markers Levels

Tumor cells release an increased amount of certain factors (hereinafter "tumor specific markers") than their normal counterparts. For example, plasminogen activator (PA) is released from human glioma at a higher level than from normal brain cells (see, e.g., Gullino, *Angiogenesis, tumor vascularization, and potential interference with tumor growth*. In Mihich (ed.): "Biological Responses in Cancer." New York, Academic Press, pp. 178–184 (1985)). Similarly, tumor angiogenesis factor (TAF) is released at a higher level in tumor cells than their normal counterparts. See, e.g., Folkman, Angiogenesis and cancer, *Sem Cancer Biol*. (1992)).

Tumor specific markers can be assayed to identify SAK modulators which decrease the level of release of these markers from host cells. Typically, transformed or tumorigenic host cells are used. Various techniques which measure the release of these factors are described in Freshney (1994), supra. Also, see, Unkless et al., *J. Biol. Chem.* 249:4295–4305 (1974); Strickland & Beers, *J. Biol. Chem.* 251:5694–5702 (1976); Whur et al., *Br. J. Cancer* 42:305–312 (1980); Gulino, *Angiogenesis, tumor vascularization, and potential interference with tumor growth*. In Mihich, E. (ed): "Biological Responses in Cancer." New York, Plenum (1985); Freshney *Anticancer Res.* 5:111–130 (1985).

Invasiveness into Matrigel

The degree of invasiveness into Matrigel or some other extracellular matrix constituent can be used as an assay to identify SAK modulators which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used as host cells. Therefore, SAK modulators can be identified by measuring changes in the level of invasiveness between the host cells before and after the introduction of potential modulators. If a compound modulates SAK, its expression in tumorigenic host cells would affect invasiveness.

Techniques described in Freshney (1994), supra, can be used. Briefly, the level of invasion of host cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

Apoptosis Analysis

Apoptosis analysis can be used as an assay to identify SAK modulators. In this assay, cell lines, such as RKO or HCT116, can be used to screen SAK modulators. Cells are contacted with a putative SAK modulator. The cells can be co-transfected with a construct comprising a marker gene, such as a gene that encodes green fluorescent protein, or a cell tracker dye. The apoptotic change can be determined using methods known in the art, such as DAPI staining and TUNEL assay using fluorescent microscope. For TUNEL assay, commercially available kit can be used (e.g., Fluorescein FragEL DNA Fragmentation Detection Kit (Oncogene Research Products, Cat.# QIA39)+Tetramethyl-rhodamine-5-dUTP (Roche, Cat. # 1534 378)). Cells contacted with SAK modulators would exhibit, e.g., an increased apoptosis compared to control.

$G_0/G_1$ Cell Cycle Arrest Analysis $G_0/G_1$ cell cycle arrest can be used as an assay to identify SAK modulators. In this assay, cell lines, such as RKO or HCT116, can be used to screen SAK modulators. The cells can be co-transfected with a construct comprising a marker gene, such as a gene that encodes green fluorescent protein, or a cell tracker dye. Methods known in the art can be used to measure the degree of $G_1$ cell cycle arrest. For example, a propidium iodide signal can be used as a measure for DNA content to determine cell cycle profiles on a flow cytometer. The percent of the cells in each cell cycle can be calculated. Cells contacted with a SAK modulator would exhibit, e.g., a higher number of cells that are arrested in $G_0/G_1$ phase compared to control.

Tumor Growth in vivo

Effects of SAK modulators on cell growth can be tested in transgenic or immune-suppressed mice. Knock-out transgenic mice can be made, in which the endogenous SAK gene is disrupted. Such knock-out mice can be used to study effects of SAK, e.g., as a cancer model, as a means of assaying in vivo for compounds that modulate SAK, and to test the effects of restoring a wild-type or mutant SAK to a knock-out mice.

Knock-out cells and transgenic mice can be made by insertion of a marker gene or other heterologous gene into the endogenous SAK gene site in the mouse genome via homologous recombination. Such mice can also be made by substituting the endogenous SAK with a mutated version of SAK, or by mutating the endogenous SAK, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987). These knock-out mice can be used as hosts to test the effects of various SAK modulators on cell growth.

Alternatively, various immune-suppressed or immune-deficient host animals can be used. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. Hosts are treated with SAK modulators, e.g., by injection. After a suitable length of time, preferably 4–8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, SAK modulators which are capable, e.g., of inhibiting abnormal cell proliferation can be identified.

B. Modulators

The compounds tested as modulators of SAK protein can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of an SAK protein. Typically, test compounds will be small organic molecules, peptides, circular peptides, RNAi, antisense molecules, ribozymes, and lipids.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g.,. PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/ or peptidyl phosphonates (Campbell et al., *J. Org. Chem.*

59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309–314 (1996) and PCT/U.S.96/10287), carbohydrate libraries (see, e.g., Liang et al., *Science,* 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass. 433A Applied Biosystems, Foster City, Calif., 9050 Plus, Millipore, Bedford, Mass. ). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a SAK protein, or a cell or tissue expressing an SAK protein, either naturally occurring or recombinant. In another embodiment, the invention provides solid phase based in vitro assays in a high throughput format, where the SAK protein or SAK substrate is attached to a solid phase. Any one of the assays described herein can be adapted for high throughput screening.

In the high throughput assays of the invention, either soluble or solid state, it is possible to screen up to several thousand different modulators or ligands in a single day. This methodology can be used for SAK proteins in vitro, or for cell-based or membrane-based assays comprising an SAK protein. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage. A tag for covalent or non-covalent binding can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly Gly sequences of between about 5 and 200 amino acids (SEQ ID NO:8). Such flexible linkers are known to persons of skill in the art. For example, poly(ethelyne glycol) linkers are available from Shearwater Polymers, Inc. Huntsville, Alabama. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of SAK Polypeptides

In addition to the detection of SAK gene and gene expression using nucleic acid hybridization technology, one can also use immunoassays to detect SAK proteins of the invention.

Such assays are useful for screening for modulators of SAK, as well as for therapeutic and diagnostic applications. Immunoassays can be used to qualitatively or quantitatively analyze SAK protein. A general overview of the applicable technology can be found in Harlow & Lane, *Antibodies: A Laboratory Manual* (1988).

A. Production of Antibodies

Methods of producing polyclonal and monoclonal antibodies that react specifically with the SAK proteins are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al, *Science* 246:1275–1281 (1989); Ward et al., *Nature* 341:544–546 (1989)).

A number of immunogens comprising portions of SAK protein may be used to produce antibodies specifically reactive with SAK protein. For example, recombinant SAK protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-SAK proteins, using a competitive binding immunoassay. Specific polyclonal antisera and monoclonal antibodies will usually bind with a $K_d$ of at least about 0.1 mM, more usually at least about 1 µM, preferably at least about 0.1 µM or better, and most preferably, 0.01 µM or better. Antibodies specific only for a particular SAK ortholog, such as human SAK, can also be made, by subtracting out other cross-reacting orthologs from a species such as a non-human mammal. In this manner, antibodies that bind only to SAK protein may be obtained.

Once the specific antibodies against SAK protein are available, the protein can be detected by a variety of immunoassay methods. In addition, the antibody can be used therapeutically as a SAK modulators. For a review of immunological and immunoassay procedures, see *Basic and Clinical Immunology* (Stites & Terr eds., 7th ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

SAK protein can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the SAK protein or antigenic subsequence thereof). The antibody (e.g., anti-SAK) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled SAK or a labeled anti-SAK antibody. Alternatively, the labeling agent may be a third moiety, such a secondary antibody, that specifically binds to the antibody/SAK complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting SAK in samples may be either competitive or noncompetitive. Noncompetitive immunoassays are assays in which the amount of antigen is directly measured. In one preferred "sandwich" assay, for example, the anti-SAK antibodies can be bound directly to a solid substrate on which they are immobilized. These immobilized antibodies then capture SAK present in the test sample. SAK proteins thus immobilized are then bound by a labeling agent, such as a second SAK antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of SAK protein present in the sample is measured indirectly by measuring the amount of a known, added (exogenous) SAK protein displaced (competed away) from an anti-SAK antibody by the unknown SAK protein present in a sample. In one competitive assay, a known amount of SAK protein is added to a sample and the sample is then contacted with an antibody that specifically binds to SAK protein. The amount of exogenous SAK protein bound to the antibody is inversely proportional to the concentration of SAK protein present in the sample. In a particularly preferred embodiment, the antibody is immobilized on a solid substrate. The amount of SAK protein bound to the antibody may be determined either by measuring the amount of SAK present in SAK protein/antibody complex, or alternatively by measuring the amount of remaining uncomplexed protein. The amount of SAK protein may be detected by providing a labeled SAK molecule.

A hapten inhibition assay is another preferred competitive assay. In this assay the known SAK protein is immobilized on a solid substrate. A known amount of anti-SAK antibody is added to the sample, and the sample is then contacted with the immobilized SAK. The amount of anti-SAK antibody bound to the known immobilized SAK is inversely proportional to the amount of SAK protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for crossreactivity determinations. For example, an SAK protein can be immobilized to a solid support. Proteins (e.g., SAK and homologs) are added to the assay that compete for binding of the antisera to the immobilized antigen. The ability of the added proteins to compete for binding of the antisera to the immobilized protein is compared to the ability of the SAK protein to compete with itself. The percent cross-reactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of an SAK protein, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the SAK protein that is required to inhibit 50% of binding, then the second protein is said to specifically bind to the polyclonal antibodies generated to SAK immunogen.

Other Assay Formats

Western blot (immunoblot) analysis is used to detect and quantify the presence of SAK in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind SAK. The anti-SAK antibodies specifically bind to the SAK on the solid support. These antibodies may be directly labeled or alternatively may be subsequently detected using labeled antibodies (e.g., labeled sheep anti-mouse antibodies) that specifically bind to the anti-SAK antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34–41 (1986)).

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize SAK protein, or secondary antibodies that recognize anti-SAK.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Cellular Transfection and Gene Therapy

The present invention provides the nucleic acids of SAK protein for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a SAK protein of the present invention, thereby mitigating the effects of absent, partial inactivation, or abnormal expression of an SAK gene, particularly as it relates to cellular proliferation. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects, cancer, and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357:455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1:13–26 (1994)).

Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the SAK protein, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

EXAMPLES

The following examples are offered to illustrate, but not to limit the claimed invention.

Example 1

Identification of SAK Using Proteomics Assay and Role of SAK in Modulation of Cellular and Tumor Cell Proliferation Mass spectrometric analysis of hits generated in immunoprecipitation with antibodies specific to Chk2 "bait" were used to identify molecules involved in cell cycle regulation. SAK was shown to bind to Chk2 after a Chk2-SAK complex was isolated from a binding assay using immunoprecipitation with an anti-Chk2 antibody, and analyzed using mass spectroscopy. As shown in FIGS. 2–11, dominant negative studies with mutant SAK shown that mutant SAK has a stronger antiproliferative phenotype than wild type SAK in tumor cells, while neither wild type nor mutant SAK is antiproliferative in normal cells (using, e.g., GFP positivity and cell tracker assays). FIGS. 12–13 demonstrate that inhibition of SAK mRNA with antisense oligos is antiproliferative in A549 tumor cells and HeLa cells. Furthermore, FIG. 14 shows that SAK mRNA is overexpressed in some tumor cell lines. These functional studies demonstrate that inhibition of SAK will inhibit tumor cell growth.

Example 2

Assay for SAK Kinase Activity

Samples include TRA-dGFP, TRA-SAK wt, TRA-SAK K41M, and mock. The SAK kinase domain and other SAK mutants can also be used in this assay.

Cells are transfected with nucleic acids encoding the sample proteins using $Ca^{2+}$ transfection, and incubated for 24 hours. The cells are treated with Nocodiazole for 18 hours, with a 2 hour release. The cells are lysed using a lysis buffer comprising 50 mM HEPES pH 7.4, 1% Triton, proteinase inhibitors, phosphatase inhibitors, EDTA, and EGTA. Immunoprecipitate (e.g., with rabbit anti-GFP antibody).

Beads are washed with lysis buffer, then with kinase buffer (20 mM MOPS pH 7.2, 25 mM β-glycerol phosphate, 5 mM EGTA, 1 mM sodium orthovanadate, and 1 mM DTT. Add 30 µl kinase buffer to beads, then add Histon or MBP (substrate, 20 µg). Add $\gamma$-$^{32}$P-ATP (10 µCi (66 nM) and cold ATP (final 90 µM)/$MgCl_2$ (final 67.5 mM). Incubate for 10 minutes at room temperature, and run SDS PAGE.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

We claim:

1. A method for identifying a compound that modulates cellular proliferation, the method comprising the steps of:
   (i) contacting the compound with a SAK polypeptide, the polypeptide encoded by a nucleic acid that encodes the SAK polypeptide of SEQ ID NO:2, the polypeptide having serine/threonine kinase activity; and
   (ii) determining a functional effect of the compound upon the SAK polypeptide, wherein the functional effect is in vitro determined by measuring kinase activity of the SAK polypeptide, which indicates that the compound modulates cellular proliferation.

2. The method of claim 1, wherein modulation is inhibition of cellular proliferation.

3. The method of claim 1, wherein modulation is inhibition of cancer cell proliferation.

4. The method of claim 1, wherein the polypeptide is recombinant.

5. The method of claim 1, wherein the polypeptide is encoded by a nucleic acid comprising SEQ ID NO:1.

6. The method of claim 1, wherein the compound is an antibody.

7. The method of claim 1, wherein the compound is a small organic molecule.

8. The method of claim 1, wherein the compound is a peptide.

9. The method of claim 8, wherein the peptide is circular.

* * * * *

SEQUENCE LISTING

```
<160> NUMBER OF SEQ ID NOS: 8

<210> SEQ ID NO 1
<211> LENGTH: 2913
<212> TYPE: DNA
<213> ORGANISM: Homo sapiens
<220> FEATURE:
<221> NAME/KEY: CDS
<222> LOCATION: (1)..(2913)
<223> OTHER INFORMATION: human SAK serine/threonine kinase

<400> SEQUENCE: 1 atg gcg acc tgc atc ggg gag aag atc gag gat ttt aaa gtt gga aat      48
Met Ala Thr Cys Ile Gly Glu Lys Ile Glu Asp Phe Lys Val Gly Asn
  1               5                  10                  15 ctg ctt ggt aaa gga tca ttt gct ggt gtc tac aga gct gag tcc att      96
Leu Leu Gly Lys Gly Ser Phe Ala Gly Val Tyr Arg Ala Glu Ser Ile
```

-continued

```
                        20                      25                      30
cac act ggt ttg gaa gtt gca atc aaa atg ata gat aag aaa gcc atg       144
His Thr Gly Leu Glu Val Ala Ile Lys Met Ile Asp Lys Lys Ala Met
         35                      40                      45 tac aaa gca gga atg gta cag aga gtc caa aat gag gtg aaa ata cat       192
Tyr Lys Ala Gly Met Val Gln Arg Val Gln Asn Glu Val Lys Ile His
 50                      55                      60 tgc caa ttg aaa cat cct tct atc ttg gag ctt tat aac tat ttt gaa       240
Cys Gln Leu Lys His Pro Ser Ile Leu Glu Leu Tyr Asn Tyr Phe Glu
 65                      70                      75                  80 gat agc aat tat gtg tat ctg gta tta gaa atg tgc cat aat gga gaa       288
Asp Ser Asn Tyr Val Tyr Leu Val Leu Glu Met Cys His Asn Gly Glu
                 85                      90                      95 atg aac agg tat cta aag aat aga gtg aaa ccc ttc tca gaa aat gaa       336
Met Asn Arg Tyr Leu Lys Asn Arg Val Lys Pro Phe Ser Glu Asn Glu
            100                     105                     110 gct cga cac ttc atg cac cag atc atc aca ggg atg ttg tat ctt cat       384
Ala Arg His Phe Met His Gln Ile Ile Thr Gly Met Leu Tyr Leu His
            115                     120                     125 tct cat ggt ata cta cac cgg gac ctc aca ctt tct aac ctc cta ctg       432
Ser His Gly Ile Leu His Arg Asp Leu Thr Leu Ser Asn Leu Leu Leu
    130                     135                     140 act cgt aat atg aac atc aag att gct gat ttt ggg ctg gca act caa       480
Thr Arg Asn Met Asn Ile Lys Ile Ala Asp Phe Gly Leu Ala Thr Gln
145                     150                     155                     160 ctg aaa atg cca cat gaa aag cac tat aca tta tgt gga act cct aac       528
Leu Lys Met Pro His Glu Lys His Tyr Thr Leu Cys Gly Thr Pro Asn
                    165                     170                     175 tac att tca cca gaa att gcc act cga agt gca cat ggc ctt gaa tct       576
Tyr Ile Ser Pro Glu Ile Ala Thr Arg Ser Ala His Gly Leu Glu Ser
                180                     185                     190 gat gtt tgg tcc ctg ggc tgt atg ttt tat aca tta ctt atc ggg aga       624
Asp Val Trp Ser Leu Gly Cys Met Phe Tyr Thr Leu Leu Ile Gly Arg
            195                     200                     205 cca ccc ttc gac act gac aca gtc aag aac aca tta aat aaa gta gta       672
Pro Pro Phe Asp Thr Asp Thr Val Lys Asn Thr Leu Asn Lys Val Val
    210                     215                     220 ttg gca gat tat gaa atg cca tct ttt ttg tca ata gag gcc aag gac       720
Leu Ala Asp Tyr Glu Met Pro Ser Phe Leu Ser Ile Glu Ala Lys Asp
225                     230                     235                     240 ctt att cac cag tta ctt cgt aga aat cca gca gat cgt tta agt ctg       768
Leu Ile His Gln Leu Leu Arg Arg Asn Pro Ala Asp Arg Leu Ser Leu
                    245                     250                     255 tct tca gta ttg gac cat cct ttt atg tcc cga aat tct tca aca aaa       816
Ser Ser Val Leu Asp His Pro Phe Met Ser Arg Asn Ser Ser Thr Lys
                260                     265                     270 agt aaa gat tta gga act gtg gaa gac tca att gat agt ggg cat gcc       864
Ser Lys Asp Leu Gly Thr Val Glu Asp Ser Ile Asp Ser Gly His Ala
            275                     280                     285 aca att tct act gca att aca gct tct tcc agt acc agt ata agt ggt       912
Thr Ile Ser Thr Ala Ile Thr Ala Ser Ser Ser Thr Ser Ile Ser Gly
    290                     295                     300 agt tta ttt gac aaa aga aga ctt ttg att ggt cag cca ctc cca aat       960
Ser Leu Phe Asp Lys Arg Arg Leu Leu Ile Gly Gln Pro Leu Pro Asn
305                     310                     315                     320 aaa atg act gta ttt cca aag aat aaa agt tca act gat ttt tct tct      1008
Lys Met Thr Val Phe Pro Lys Asn Lys Ser Ser Thr Asp Phe Ser Ser
                    325                     330                     335 tca gga gat gga aac agt ttt tat act cag tgg gga aat caa gaa acc      1056
```

```
Ser Gly Asp Gly Asn Ser Phe Tyr Thr Gln Trp Gly Asn Gln Glu Thr
            340                 345                 350 agt aat agt gga agg gga aga gta att caa gat gca gaa gaa agg cca      1104
Ser Asn Ser Gly Arg Gly Arg Val Ile Gln Asp Ala Glu Glu Arg Pro
            355                 360                 365 cat tct cga tac ctt cgt aga gct tat tcc tct gat aga tct ggc act      1152
His Ser Arg Tyr Leu Arg Arg Ala Tyr Ser Ser Asp Arg Ser Gly Thr
            370                 375                 380 tct aat agt cag tct caa gca aaa aca tat aca atg gaa cga tgt cac      1200
Ser Asn Ser Gln Ser Gln Ala Lys Thr Tyr Thr Met Glu Arg Cys His
385                 390                 395                 400 tca gca gaa atg ctt tca gtg tcc aaa aga tca gga gga ggt gaa aat      1248
Ser Ala Glu Met Leu Ser Val Ser Lys Arg Ser Gly Gly Gly Glu Asn
                405                 410                 415 gaa gag agg tac tca ccc aca gac aac aat gcc aac att ttt aac ttc      1296
Glu Glu Arg Tyr Ser Pro Thr Asp Asn Asn Ala Asn Ile Phe Asn Phe
            420                 425                 430 ttt aaa gaa aag aca tcc agt agt tct gga tct ttt gaa aga cct gat      1344
Phe Lys Glu Lys Thr Ser Ser Ser Ser Gly Ser Phe Glu Arg Pro Asp
            435                 440                 445 aac aat caa gca ctc tcc aat cat ctt tgt cca gga aaa act cct ttt      1392
Asn Asn Gln Ala Leu Ser Asn His Leu Cys Pro Gly Lys Thr Pro Phe
            450                 455                 460 cca ttt gca gac ccg aca cct cag act gaa acc gta caa cag tgg ttt      1440
Pro Phe Ala Asp Pro Thr Pro Gln Thr Glu Thr Val Gln Gln Trp Phe
465                 470                 475                 480 ggg aat ctg caa ata aat gct cat tta aga aaa act act gaa tat gac      1488
Gly Asn Leu Gln Ile Asn Ala His Leu Arg Lys Thr Thr Glu Tyr Asp
                485                 490                 495 agc atc agc cca aac cgg gac ttc cag ggc cat cca gat ttg cag aag      1536
Ser Ile Ser Pro Asn Arg Asp Phe Gln Gly His Pro Asp Leu Gln Lys
            500                 505                 510 gac aca tca aaa aat gcc tgg act gat aca aaa gtc aaa aag aac tct      1584
Asp Thr Ser Lys Asn Ala Trp Thr Asp Thr Lys Val Lys Lys Asn Ser
            515                 520                 525 gat gct tct gat aat gca cat tct gta aaa cag caa aat acc atg aaa      1632
Asp Ala Ser Asp Asn Ala His Ser Val Lys Gln Gln Asn Thr Met Lys
530                 535                 540 tat atg act gca ctt cac agt aaa cct gag ata atc caa caa gaa tgt      1680
Tyr Met Thr Ala Leu His Ser Lys Pro Glu Ile Ile Gln Gln Glu Cys
545                 550                 555                 560 gtt ttt ggc tca gat cct ctt tct gaa cag agc aag act agg ggt atg      1728
Val Phe Gly Ser Asp Pro Leu Ser Glu Gln Ser Lys Thr Arg Gly Met
                565                 570                 575 gag cca cca tgg ggt tat cag aat cgt aca tta aga agc att aca tct      1776
Glu Pro Pro Trp Gly Tyr Gln Asn Arg Thr Leu Arg Ser Ile Thr Ser
            580                 585                 590 ccg ttg gtt gct cac agg tta aaa cca atc aga cag aaa acc aaa aag      1824
Pro Leu Val Ala His Arg Leu Lys Pro Ile Arg Gln Lys Thr Lys Lys
            595                 600                 605 gct gtg gtg agc ata ctt gat tca gag gag gtg tgt gtg gag ctt gta      1872
Ala Val Val Ser Ile Leu Asp Ser Glu Glu Val Cys Val Glu Leu Val
            610                 615                 620 aag gag tat gca tct caa gaa tat gtg aaa gaa gtt ctt cag ata tct      1920
Lys Glu Tyr Ala Ser Gln Glu Tyr Val Lys Glu Val Leu Gln Ile Ser
625                 630                 635                 640 agt gat gga aat acg atc act att tat tat cca aat ggt ggt aga ggt      1968
Ser Asp Gly Asn Thr Ile Thr Ile Tyr Tyr Pro Asn Gly Gly Arg Gly
                645                 650                 655
```

```
                                                   -continued ttt cct ctt gct gat aga cca ccc tca cct act gac aac atc agt agg     2016
Phe Pro Leu Ala Asp Arg Pro Pro Ser Pro Thr Asp Asn Ile Ser Arg
            660                 665                 670 tac agc ttt gac aat tta cca gaa aaa tac tgg cga aaa tat caa tat     2064
Tyr Ser Phe Asp Asn Leu Pro Glu Lys Tyr Trp Arg Lys Tyr Gln Tyr
        675                 680                 685 gct tcc agg ttt gta cag ctt gta aga tct aaa tct ccc aaa atc act     2112
Ala Ser Arg Phe Val Gln Leu Val Arg Ser Lys Ser Pro Lys Ile Thr
690                 695                 700 tat ttt aca aga tat gct aaa tgc att ttg atg gag aat tct cct ggt     2160
Tyr Phe Thr Arg Tyr Ala Lys Cys Ile Leu Met Glu Asn Ser Pro Gly
705                 710                 715                 720 gct gat ttt gag gtt tgg ttt tat gat ggg gta aaa ata cac aaa aca     2208
Ala Asp Phe Glu Val Trp Phe Tyr Asp Gly Val Lys Ile His Lys Thr
            725                 730                 735 gaa gat ttc att cag gtg att gaa aag aca ggg aag tct tac act tta     2256
Glu Asp Phe Ile Gln Val Ile Glu Lys Thr Gly Lys Ser Tyr Thr Leu
        740                 745                 750 aaa agt gaa agt gaa gtt aat agc ttg aaa gag gag ata aaa atg tat     2304
Lys Ser Glu Ser Glu Val Asn Ser Leu Lys Glu Glu Ile Lys Met Tyr
    755                 760                 765 atg gac cat gct aat gag ggt cat cgt att tgt tta gca ctg gaa tcc     2352
Met Asp His Ala Asn Glu Gly His Arg Ile Cys Leu Ala Leu Glu Ser
770                 775                 780 ata att tca gaa gag gaa agg aaa act agg agt gct ccc ttt ttc cca     2400
Ile Ile Ser Glu Glu Glu Arg Lys Thr Arg Ser Ala Pro Phe Phe Pro
785                 790                 795                 800 ata atc ata gga aga aaa cct ggt agt act agt tca cct aag gcc tta     2448
Ile Ile Ile Gly Arg Lys Pro Gly Ser Thr Ser Ser Pro Lys Ala Leu
            805                 810                 815 tca cct cct cct tct gtg gat tca aat tac cca acg aga gat aga gca     2496
Ser Pro Pro Pro Ser Val Asp Ser Asn Tyr Pro Thr Arg Asp Arg Ala
        820                 825                 830 tct ttc aac aga atg gtc atg cat agt gct gct tct cca aca cag gca     2544
Ser Phe Asn Arg Met Val Met His Ser Ala Ala Ser Pro Thr Gln Ala
    835                 840                 845 cca atc ctt aat ccc tct atg gtt aca aat gaa gga ctt ggt ctt aca     2592
Pro Ile Leu Asn Pro Ser Met Val Thr Asn Glu Gly Leu Gly Leu Thr
850                 855                 860 act aca gct tct gga aca gac atc tct tct aat agt cta aaa gat tgt     2640
Thr Thr Ala Ser Gly Thr Asp Ile Ser Ser Asn Ser Leu Lys Asp Cys
865                 870                 875                 880 ctt cct aaa tca gca caa ctt ttg aaa tct gtt ttt gtg aaa aat gtt     2688
Leu Pro Lys Ser Ala Gln Leu Leu Lys Ser Val Phe Val Lys Asn Val
            885                 890                 895 ggt tgg gct aca cag tta act agt gga gct gtg tgg gtt cag ttt aat     2736
Gly Trp Ala Thr Gln Leu Thr Ser Gly Ala Val Trp Val Gln Phe Asn
        900                 905                 910 gat ggg tcc cag ttg gtt gtg cag gca gga gtg tct tct atc agt tat     2784
Asp Gly Ser Gln Leu Val Val Gln Ala Gly Val Ser Ser Ile Ser Tyr
    915                 920                 925 acc tca cca aat ggt caa aca act agg tat gga gaa aat gaa aaa tta     2832
Thr Ser Pro Asn Gly Gln Thr Thr Arg Tyr Gly Glu Asn Glu Lys Leu
930                 935                 940 cca gac tac atc aaa cag aaa tta cag tgt ctg tct tcc atc ctt ttg     2880
Pro Asp Tyr Ile Lys Gln Lys Leu Gln Cys Leu Ser Ser Ile Leu Leu
945                 950                 955                 960 atg ttt tct aat ccg act cct aat ttt cat tga                         2913
Met Phe Ser Asn Pro Thr Pro Asn Phe His
            965                 970
```

<210> SEQ ID NO 2
<211> LENGTH: 970
<212> TYPE: PRT
<213> ORGANISM: Homo sapiens
<220> FEATURE:
<223> OTHER INFORMATION: human SAK serine/threonine kinase

<400> SEQUENCE: 2

```
Met Ala Thr Cys Ile Gly Glu Lys Ile Glu Asp Phe Lys Val Gly Asn
  1               5                  10                  15

Leu Leu Gly Lys Gly Ser Phe Ala Gly Val Tyr Arg Ala Glu Ser Ile
             20                  25                  30

His Thr Gly Leu Glu Val Ala Ile Lys Met Ile Asp Lys Lys Ala Met
         35                  40                  45

Tyr Lys Ala Gly Met Val Gln Arg Val Gln Asn Glu Val Lys Ile His
     50                  55                  60

Cys Gln Leu Lys His Pro Ser Ile Leu Glu Leu Tyr Asn Tyr Phe Glu
 65                  70                  75                  80

Asp Ser Asn Tyr Val Tyr Leu Val Leu Glu Met Cys His Asn Gly Glu
                 85                  90                  95

Met Asn Arg Tyr Leu Lys Asn Arg Val Lys Pro Phe Ser Glu Asn Glu
            100                 105                 110

Ala Arg His Phe Met His Gln Ile Ile Thr Gly Met Leu Tyr Leu His
        115                 120                 125

Ser His Gly Ile Leu His Arg Asp Leu Thr Leu Ser Asn Leu Leu Leu
    130                 135                 140

Thr Arg Asn Met Asn Ile Lys Ile Ala Asp Phe Gly Leu Ala Thr Gln
145                 150                 155                 160

Leu Lys Met Pro His Glu Lys His Tyr Thr Leu Cys Gly Thr Pro Asn
                165                 170                 175

Tyr Ile Ser Pro Glu Ile Ala Thr Arg Ser Ala His Gly Leu Glu Ser
            180                 185                 190

Asp Val Trp Ser Leu Gly Cys Met Phe Tyr Thr Leu Leu Ile Gly Arg
        195                 200                 205

Pro Pro Phe Asp Thr Asp Thr Val Lys Asn Thr Leu Asn Lys Val Val
    210                 215                 220

Leu Ala Asp Tyr Glu Met Pro Ser Phe Leu Ser Ile Glu Ala Lys Asp
225                 230                 235                 240

Leu Ile His Gln Leu Leu Arg Arg Asn Pro Ala Asp Arg Leu Ser Leu
                245                 250                 255

Ser Ser Val Leu Asp His Pro Phe Met Ser Arg Asn Ser Ser Thr Lys
            260                 265                 270

Ser Lys Asp Leu Gly Thr Val Glu Asp Ser Ile Asp Ser Gly His Ala
        275                 280                 285

Thr Ile Ser Thr Ala Ile Thr Ala Ser Ser Ser Thr Ser Ile Ser Gly
    290                 295                 300

Ser Leu Phe Asp Lys Arg Arg Leu Leu Ile Gly Gln Pro Leu Pro Asn
305                 310                 315                 320

Lys Met Thr Val Phe Pro Lys Asn Lys Ser Ser Thr Asp Phe Ser Ser
                325                 330                 335

Ser Gly Asp Gly Asn Ser Phe Tyr Thr Gln Trp Gly Asn Gln Glu Thr
            340                 345                 350

Ser Asn Ser Gly Arg Gly Arg Val Ile Gln Asp Ala Glu Glu Arg Pro
        355                 360                 365
```

```
His Ser Arg Tyr Leu Arg Arg Ala Tyr Ser Ser Asp Arg Ser Gly Thr
    370                 375                 380

Ser Asn Ser Gln Ser Gln Ala Lys Thr Tyr Thr Met Glu Arg Cys His
385                 390                 395                 400

Ser Ala Glu Met Leu Ser Val Ser Lys Arg Ser Gly Gly Gly Glu Asn
                405                 410                 415

Glu Glu Arg Tyr Ser Pro Thr Asp Asn Ala Asn Ile Phe Asn Phe
            420                 425                 430

Phe Lys Glu Lys Thr Ser Ser Ser Gly Ser Phe Glu Arg Pro Asp
        435                 440                 445

Asn Asn Gln Ala Leu Ser Asn His Leu Cys Pro Gly Lys Thr Pro Phe
    450                 455                 460

Pro Phe Ala Asp Pro Thr Pro Gln Thr Glu Thr Val Gln Gln Trp Phe
465                 470                 475                 480

Gly Asn Leu Gln Ile Asn Ala His Leu Arg Lys Thr Thr Glu Tyr Asp
                485                 490                 495

Ser Ile Ser Pro Asn Arg Asp Phe Gln Gly His Pro Asp Leu Gln Lys
            500                 505                 510

Asp Thr Ser Lys Asn Ala Trp Thr Asp Thr Lys Val Lys Lys Asn Ser
        515                 520                 525

Asp Ala Ser Asp Asn Ala His Ser Val Lys Gln Asn Thr Met Lys
    530                 535                 540

Tyr Met Thr Ala Leu His Ser Lys Pro Glu Ile Ile Gln Gln Glu Cys
545                 550                 555                 560

Val Phe Gly Ser Asp Pro Leu Ser Glu Gln Ser Lys Thr Arg Gly Met
                565                 570                 575

Glu Pro Pro Trp Gly Tyr Gln Asn Arg Thr Leu Arg Ser Ile Thr Ser
            580                 585                 590

Pro Leu Val Ala His Arg Leu Lys Pro Ile Arg Gln Lys Thr Lys Lys
        595                 600                 605

Ala Val Val Ser Ile Leu Asp Ser Glu Glu Val Cys Val Glu Leu Val
    610                 615                 620

Lys Glu Tyr Ala Ser Gln Glu Tyr Val Lys Glu Val Leu Gln Ile Ser
625                 630                 635                 640

Ser Asp Gly Asn Thr Ile Thr Ile Tyr Tyr Pro Asn Gly Gly Arg Gly
                645                 650                 655

Phe Pro Leu Ala Asp Arg Pro Pro Ser Pro Thr Asp Asn Ile Ser Arg
            660                 665                 670

Tyr Ser Phe Asp Asn Leu Pro Glu Lys Tyr Trp Arg Lys Tyr Gln Tyr
        675                 680                 685

Ala Ser Arg Phe Val Gln Leu Val Arg Ser Lys Ser Pro Lys Ile Thr
    690                 695                 700

Tyr Phe Thr Arg Tyr Ala Lys Cys Ile Leu Met Glu Asn Ser Pro Gly
705                 710                 715                 720

Ala Asp Phe Glu Val Trp Phe Tyr Asp Gly Val Lys Ile His Lys Thr
                725                 730                 735

Glu Asp Phe Ile Gln Val Ile Glu Lys Thr Gly Lys Ser Tyr Thr Leu
            740                 745                 750

Lys Ser Glu Ser Glu Val Asn Ser Leu Lys Glu Ile Lys Met Tyr
        755                 760                 765

Met Asp His Ala Asn Glu Gly His Arg Ile Cys Leu Ala Leu Glu Ser
    770                 775                 780
```

```
Ile Ile Ser Glu Glu Arg Lys Thr Arg Ser Ala Pro Phe Phe Pro
785                 790                 795                 800

Ile Ile Ile Gly Arg Lys Pro Gly Ser Thr Ser Ser Pro Lys Ala Leu
            805                 810                 815

Ser Pro Pro Ser Val Asp Ser Asn Tyr Pro Thr Arg Asp Arg Ala
        820                 825                 830

Ser Phe Asn Arg Met Val Met His Ser Ala Ala Ser Pro Thr Gln Ala
        835                 840                 845

Pro Ile Leu Asn Pro Ser Met Val Thr Asn Glu Gly Leu Gly Leu Thr
850                 855                 860

Thr Thr Ala Ser Gly Thr Asp Ile Ser Ser Asn Ser Leu Lys Asp Cys
865                 870                 875                 880

Leu Pro Lys Ser Ala Gln Leu Leu Lys Ser Val Phe Val Lys Asn Val
                885                 890                 895

Gly Trp Ala Thr Gln Leu Thr Ser Gly Ala Val Trp Val Gln Phe Asn
                900                 905                 910

Asp Gly Ser Gln Leu Val Val Gln Ala Gly Val Ser Ser Ile Ser Tyr
            915                 920                 925

Thr Ser Pro Asn Gly Gln Thr Thr Arg Tyr Gly Glu Asn Glu Lys Leu
    930                 935                 940

Pro Asp Tyr Ile Lys Gln Lys Leu Gln Cys Leu Ser Ser Ile Leu Leu
945                 950                 955                 960

Met Phe Ser Asn Pro Thr Pro Asn Phe His
                965                 970

<210> SEQ ID NO 3
<211> LENGTH: 379
<212> TYPE: PRT
<213> ORGANISM: Homo sapiens
<220> FEATURE:
<221> NAME/KEY: DOMAIN
<222> LOCATION: (1)..(379)
<223> OTHER INFORMATION: SAK serine/threonine kinase kinase domain

<400> SEQUENCE: 3

Met Ala Thr Cys Ile Gly Glu Lys Ile Glu Asp Phe Lys Val Gly Asn
1               5                   10                  15

Leu Leu Gly Lys Gly Ser Phe Ala Gly Val Tyr Arg Ala Glu Ser Ile
            20                  25                  30

His Thr Gly Leu Glu Val Ala Ile Lys Met Ile Asp Lys Lys Ala Met
        35                  40                  45

Tyr Lys Ala Gly Met Val Gln Arg Val Gln Asn Glu Val Lys Ile His
    50                  55                  60

Cys Gln Leu Lys His Pro Ser Ile Leu Glu Leu Tyr Asn Tyr Phe Glu
65                  70                  75                  80

Asp Ser Asn Tyr Val Tyr Leu Val Leu Glu Met Cys His Asn Gly Glu
                85                  90                  95

Met Asn Arg Tyr Leu Lys Asn Arg Val Lys Pro Phe Ser Glu Asn Glu
            100                 105                 110

Ala Arg His Phe Met His Gln Ile Ile Thr Gly Met Leu Tyr Leu His
        115                 120                 125

Ser His Gly Ile Leu His Arg Asp Leu Thr Leu Ser Asn Leu Leu Leu
    130                 135                 140

Thr Arg Asn Met Asn Ile Lys Ile Ala Asp Phe Gly Leu Ala Thr Gln
145                 150                 155                 160

Leu Lys Met Pro His Glu Lys His Tyr Thr Leu Cys Gly Thr Pro Asn
```

-continued

```
                    165                 170                 175
Tyr Ile Ser Pro Glu Ile Ala Thr Arg Ser Ala His Gly Leu Glu Ser
                180                 185                 190

Asp Val Trp Ser Leu Gly Cys Met Phe Tyr Thr Leu Leu Ile Gly Arg
            195                 200                 205

Pro Pro Phe Asp Thr Asp Thr Val Lys Asn Thr Leu Asn Lys Val Val
        210                 215                 220

Leu Ala Asp Tyr Glu Met Pro Ser Phe Leu Ser Ile Glu Ala Lys Asp
225                 230                 235                 240

Leu Ile His Gln Leu Leu Arg Arg Asn Pro Ala Asp Arg Leu Ser Leu
                245                 250                 255

Ser Ser Val Leu Asp His Pro Phe Met Ser Arg Asn Ser Ser Thr Lys
            260                 265                 270

Ser Lys Asp Leu Gly Thr Val Glu Asp Ser Ile Asp Ser Gly His Ala
        275                 280                 285

Thr Ile Ser Thr Ala Ile Thr Ala Ser Ser Ser Thr Ser Ile Ser Gly
290                 295                 300

Ser Leu Phe Asp Lys Arg Arg Leu Leu Ile Gly Gln Pro Leu Pro Asn
305                 310                 315                 320

Lys Met Thr Val Phe Pro Lys Asn Lys Ser Ser Thr Asp Phe Ser Ser
                325                 330                 335

Ser Gly Asp Gly Asn Ser Phe Tyr Thr Gln Trp Gly Asn Gln Glu Thr
            340                 345                 350

Ser Asn Ser Gly Arg Gly Arg Val Ile Gln Asp Ala Glu Glu Arg Pro
        355                 360                 365

His Ser Arg Tyr Leu Arg Arg Ala Tyr Ser Ser
    370                 375
```

<210> SEQ ID NO 4
<211> LENGTH: 373
<212> TYPE: PRT
<213> ORGANISM: Homo sapiens
<220> FEATURE:
<221> NAME/KEY: DOMAIN
<222> LOCATION: (1)..(373)
<223> OTHER INFORMATION: human FNK mitotic kinase kinase domain

<400> SEQUENCE: 4

```
Met Glu Pro Ala Ala Gly Phe Leu Ser Pro Arg Pro Phe Gln Arg Thr
1               5                   10                  15

Ala Ala Ala Thr Ala Pro Pro Ala Gly Pro Gly Pro Pro Pro Ser Ala
                20                  25                  30

Leu Arg Gly Pro Glu Leu Glu Met Leu Ala Gly Leu Pro Thr Ser Asp
            35                  40                  45

Pro Gly Arg Leu Ile Thr Asp Pro Arg Ser Gly Arg Thr Tyr Leu Lys
        50                  55                  60

Gly Arg Leu Leu Gly Lys Gly Gly Phe Ala Arg Cys Tyr Glu Ala Thr
65                  70                  75                  80

Asp Thr Glu Thr Gly Ser Ala Tyr Ala Val Lys Val Ile Pro Gln Ser
                85                  90                  95

Arg Val Val Lys Pro His Gln Arg Glu Lys Ile Leu Asn Glu Ile Glu
            100                 105                 110

Leu His Arg Asp Leu Gln His Arg His Ile Val Arg Phe Ser His His
        115                 120                 125

Phe Glu Asp Ala Asp Asn Ile Tyr Ile Phe Leu Glu Leu Cys Ser Arg
    130                 135                 140
```

```
Lys Ser Leu Ala His Ile Trp Lys Ala Arg His Thr Leu Leu Glu Pro
145                 150                 155                 160

Glu Val Arg Tyr Tyr Leu Arg Gln Ile Leu Ser Gly Leu Lys Tyr Leu
                165                 170                 175

His Gln Arg Gly Ile Leu His Arg Asp Leu Lys Leu Gly Asn Phe Phe
            180                 185                 190

Ile Thr Glu Asn Met Glu Leu Lys Val Gly Asp Phe Gly Leu Ala Ala
        195                 200                 205

Arg Leu Glu Pro Pro Glu Gln Arg Lys Lys Thr Ile Cys Gly Thr Pro
210                 215                 220

Asn Tyr Val Ala Pro Glu Val Leu Leu Arg Gln Gly His Gly Pro Glu
225                 230                 235                 240

Ala Asp Val Trp Ser Leu Gly Cys Val Met Tyr Thr Leu Leu Cys Gly
                245                 250                 255

Ser Pro Pro Phe Glu Thr Ala Asp Leu Lys Glu Thr Tyr Arg Cys Ile
            260                 265                 270

Lys Gln Val His Tyr Thr Leu Pro Ala Ser Leu Ser Leu Pro Ala Arg
        275                 280                 285

Gln Leu Leu Ala Ala Ile Leu Arg Ala Ser Pro Arg Asp Arg Pro Ser
290                 295                 300

Ile Asp Gln Ile Leu Arg His Asp Phe Phe Thr Lys Gly Tyr Thr Pro
305                 310                 315                 320

Asp Arg Leu Pro Ile Ser Ser Cys Val Thr Val Pro Asp Leu Thr Pro
                325                 330                 335

Pro Asn Pro Ala Arg Ser Leu Phe Ala Lys Val Thr Lys Ser Leu Phe
            340                 345                 350

Val Arg Lys Lys Lys Ser Lys Asn His Ala Gln Glu Arg Asp Glu Val
        355                 360                 365

Ser Gly Leu Val Ser
        370

<210> SEQ ID NO 5
<211> LENGTH: 400
<212> TYPE: PRT
<213> ORGANISM: Homo sapiens
<220> FEATURE:
<221> NAME/KEY: DOMAIN
<222> LOCATION: (1)..(400)
<223> OTHER INFORMATION: human SNK mitotic kinase kinase domain

<400> SEQUENCE: 5

Met Glu Leu Leu Arg Thr Ile Thr Tyr Gln Pro Ala Ala Ser Thr Lys
1               5                   10                  15

Met Cys Glu Gln Ala Leu Gly Lys Gly Cys Gly Gly Asp Ser Lys Lys
            20                  25                  30

Lys Arg Pro Pro Gln Pro Pro Glu Glu Ser Gln Pro Gln Ser Gln
        35                  40                  45

Ala Gln Val Pro Pro Ala Ala Pro His His His His His Ser His
    50                  55                  60

Ser Gly Pro Glu Ile Ser Arg Ile Ile Val Asp Pro Thr Thr Gly Lys
65                  70                  75                  80

Arg Tyr Cys Arg Gly Lys Val Leu Gly Lys Gly Gly Phe Ala Lys Cys
                85                  90                  95

Tyr Glu Met Thr Asp Leu Thr Asn Asn Lys Val Tyr Ala Ala Lys Ile
            100                 105                 110
```

-continued

```
Ile Pro His Ser Arg Val Ala Lys Pro His Gln Arg Glu Lys Ile Asp
            115                 120                 125

Lys Glu Ile Glu Leu His Arg Ile Leu His His Lys His Val Val Gln
        130                 135                 140

Phe Tyr His Tyr Phe Glu Asp Lys Glu Asn Ile Tyr Ile Leu Leu Glu
145                 150                 155                 160

Tyr Cys Ser Arg Arg Ser Met Ala His Ile Leu Lys Ala Arg Lys Val
                165                 170                 175

Leu Thr Glu Pro Glu Val Arg Tyr Tyr Leu Arg Gln Ile Val Ser Gly
            180                 185                 190

Leu Lys Tyr Leu His Glu Gln Glu Ile Leu His Arg Asp Leu Lys Leu
        195                 200                 205

Gly Asn Phe Phe Ile Asn Glu Ala Met Glu Leu Lys Val Gly Asp Phe
    210                 215                 220

Gly Leu Ala Ala Arg Leu Glu Pro Leu Glu His Arg Arg Arg Thr Ile
225                 230                 235                 240

Cys Gly Thr Pro Asn Tyr Leu Ser Pro Glu Val Leu Asn Lys Gln Gly
                245                 250                 255

His Gly Cys Glu Ser Asp Ile Trp Ala Leu Gly Cys Val Met Tyr Thr
            260                 265                 270

Met Leu Leu Gly Arg Pro Pro Phe Glu Thr Thr Asn Leu Lys Glu Thr
        275                 280                 285

Tyr Arg Cys Ile Arg Glu Ala Arg Tyr Thr Met Pro Ser Ser Leu Leu
    290                 295                 300

Ala Pro Ala Lys His Leu Ile Ala Ser Met Leu Ser Lys Asn Pro Glu
305                 310                 315                 320

Asp Arg Pro Ser Leu Asp Asp Ile Ile Arg His Asp Phe Phe Leu Gln
                325                 330                 335

Gly Phe Thr Pro Asp Arg Leu Ser Ser Ser Cys Cys His Thr Val Pro
            340                 345                 350

Asp Phe His Leu Ser Ser Pro Ala Lys Asn Phe Phe Lys Lys Ala Ala
        355                 360                 365

Ala Ala Leu Phe Gly Gly Lys Lys Asp Lys Ala Arg Tyr Ile Asp Thr
    370                 375                 380

His Asn Arg Val Ser Lys Glu Asp Glu Asp Ile Tyr Lys Leu Arg His
385                 390                 395                 400
```

<210> SEQ ID NO 6
<211> LENGTH: 367
<212> TYPE: PRT
<213> ORGANISM: Homo sapiens
<220> FEATURE:
<221> NAME/KEY: DOMAIN
<222> LOCATION: (1)..(367)
<223> OTHER INFORMATION: human PLK1 mitotic kinase kinase domain

<400> SEQUENCE: 6

```
Met Ser Ala Ala Val Thr Ala Gly Lys Leu Ala Arg Ala Pro Ala Asp
  1               5                  10                  15

Pro Gly Lys Ala Gly Val Pro Gly Val Ala Ala Pro Gly Ala Pro Ala
            20                  25                  30

Ala Ala Pro Pro Ala Lys Glu Ile Pro Glu Val Leu Val Asp Pro Arg
        35                  40                  45

Ser Arg Arg Arg Tyr Val Arg Gly Arg Phe Leu Gly Lys Gly Gly Phe
    50                  55                  60

Ala Lys Cys Phe Glu Ile Ser Asp Ala Asp Thr Lys Glu Val Phe Ala
```

```
                65                  70                  75                  80
Gly Lys Ile Val Pro Lys Ser Leu Leu Lys Pro His Gln Arg Glu
                        85                  90                  95

Lys Met Ser Met Glu Ile Ser Ile His Arg Ser Leu Ala His Gln His
                100                 105                 110

Val Val Gly Phe His Gly Phe Phe Glu Asp Asn Asp Phe Val Phe Val
                115                 120                 125

Val Leu Glu Leu Cys Arg Arg Arg Ser Leu Leu Glu Leu His Lys Arg
        130                 135                 140

Arg Lys Ala Leu Thr Glu Pro Glu Ala Arg Tyr Tyr Leu Arg Gln Ile
145                 150                 155                 160

Val Leu Gly Cys Gln Tyr Leu His Arg Asn Arg Val Ile His Arg Asp
                165                 170                 175

Leu Lys Leu Gly Asn Leu Phe Leu Asn Glu Asp Leu Glu Val Lys Ile
                180                 185                 190

Gly Asp Phe Gly Leu Ala Thr Lys Val Glu Tyr Asp Gly Glu Arg Lys
                195                 200                 205

Lys Thr Leu Cys Gly Thr Pro Asn Tyr Ile Ala Pro Glu Val Leu Ser
        210                 215                 220

Lys Lys Gly His Ser Phe Glu Val Asp Val Trp Ser Ile Gly Cys Ile
225                 230                 235                 240

Met Tyr Thr Leu Leu Val Gly Lys Pro Pro Phe Glu Thr Ser Cys Leu
                245                 250                 255

Lys Glu Thr Tyr Leu Arg Ile Lys Lys Asn Glu Tyr Ser Ile Pro Lys
                260                 265                 270

His Ile Asn Pro Val Ala Ala Ser Leu Ile Gln Lys Met Leu Gln Thr
                275                 280                 285

Asp Pro Thr Ala Arg Pro Thr Ile Asn Glu Leu Leu Asn Asp Glu Phe
        290                 295                 300

Phe Thr Ser Gly Tyr Ile Pro Ala Arg Leu Pro Ile Thr Cys Leu Thr
305                 310                 315                 320

Ile Pro Pro Arg Phe Ser Ile Ala Pro Ser Ser Leu Asp Pro Ser Asn
                325                 330                 335

Arg Lys Pro Leu Thr Val Leu Asn Lys Gly Leu Glu Asn Pro Leu Pro
                340                 345                 350

Glu Arg Pro Arg Glu Lys Glu Glu Pro Val Val Arg Glu Thr Gly
                355                 360                 365

<210> SEQ ID NO 7
<211> LENGTH: 403
<212> TYPE: PRT
<213> ORGANISM: Homo sapiens
<220> FEATURE:
<223> OTHER INFORMATION: human ARK mitotic kinase

<400> SEQUENCE: 7

Met Asp Arg Ser Lys Glu Asn Cys Ile Ser Gly Pro Val Lys Ala Thr
1               5                   10                  15

Ala Pro Val Gly Gly Pro Lys Arg Val Leu Val Thr Gln Gln Phe Pro
                20                  25                  30

Cys Gln Asn Pro Leu Pro Val Asn Ser Gly Gln Ala Gln Arg Val Leu
        35                  40                  45

Cys Pro Ser Asn Ser Ser Gln Arg Ile Pro Leu Gln Ala Gln Lys Leu
    50                  55                  60

Val Ser Ser His Lys Pro Val Gln Asn Gln Lys Gln Lys Gln Leu Gln
```

```
                65                  70                  75                  80
Gln Thr Ser Val Pro His Pro Val Ser Arg Pro Leu Asn Asn Thr Gln
                    85                  90                  95
Lys Ser Lys Gln Pro Leu Pro Ser Ala Pro Glu Asn Asn Pro Glu Glu
                100                 105                 110
Glu Leu Ala Ser Lys Gln Lys Asn Glu Glu Ser Lys Lys Arg Gln Trp
            115                 120                 125
Ala Leu Glu Asp Phe Glu Ile Gly Arg Pro Leu Gly Lys Gly Lys Phe
        130                 135                 140
Gly Asn Val Tyr Leu Ala Arg Glu Lys Gln Ser Lys Gly Ile Leu Ala
145                 150                 155                 160
Leu Lys Val Leu Phe Lys Ala Gln Leu Glu Lys Ala Gly Val Glu His
                165                 170                 175
Gln Leu Arg Arg Glu Val Glu Ile Gln Ser His Leu Arg His Pro Asn
                180                 185                 190
Ile Leu Arg Leu Tyr Gly Tyr Phe His Asp Ala Thr Arg Val Tyr Leu
                195                 200                 205
Ile Leu Glu Tyr Ala Pro Leu Gly Thr Val Tyr Arg Glu Leu Gln Lys
        210                 215                 220
Leu Ser Lys Phe Asp Glu Gln Arg Thr Ala Thr Tyr Ile Thr Glu Leu
225                 230                 235                 240
Ala Asn Ala Leu Ser Tyr Cys His Ser Lys Arg Val Ile His Arg Asp
                245                 250                 255
Ile Lys Pro Glu Asn Leu Leu Leu Gly Ser Ala Gly Glu Leu Lys Ile
                260                 265                 270
Ala Asp Phe Gly Trp Ser Val His Ala Pro Ser Ser Arg Arg Thr Thr
            275                 280                 285
Leu Cys Gly Thr Leu Asp Tyr Leu Pro Pro Glu Met Ile Glu Gly Arg
        290                 295                 300
Met His Asp Glu Lys Val Asp Leu Trp Ser Leu Gly Val Leu Cys Tyr
305                 310                 315                 320
Glu Phe Leu Val Gly Lys Pro Pro Phe Glu Ala Asn Thr Tyr Gln Glu
                325                 330                 335
Thr Tyr Lys Arg Ile Ser Arg Val Glu Phe Thr Phe Pro Asp Phe Val
                340                 345                 350
Thr Glu Gly Ala Arg Asp Leu Ile Ser Arg Leu Leu Lys His Asn Pro
            355                 360                 365
Ser Gln Arg Pro Met Leu Arg Glu Val Leu Glu His Pro Trp Ile Thr
        370                 375                 380
Ala Asn Ser Ser Lys Pro Ser Asn Cys Gln Asn Lys Glu Ser Ala Ser
385                 390                 395                 400
Lys Gln Ser

<210> SEQ ID NO 8
<211> LENGTH: 200
<212> TYPE: PRT
<213> ORGANISM: Artificial Sequence
<220> FEATURE:
<223> OTHER INFORMATION: Description of Artificial Sequence:flexible
      linker
<220> FEATURE:
<221> NAME/KEY: MOD_RES
<222> LOCATION: (6)..(200)
<223> OTHER INFORMATION: Gly at positions 6-200 may be present or absent

<400> SEQUENCE: 8
```

-continued

```
Gly Gly Gly Gly Gly Gly Gly Gly Gly Gly Gly Gly Gly Gly Gly
 1           5                  10                 15
Gly Gly Gly Gly Gly Gly Gly Gly Gly Gly Gly Gly Gly Gly Gly
            20                 25                 30
Gly Gly Gly Gly Gly Gly Gly Gly Gly Gly Gly Gly Gly Gly Gly
        35                 40                 45
Gly Gly Gly Gly Gly Gly Gly Gly Gly Gly Gly Gly Gly Gly Gly
    50                 55                 60
Gly Gly Gly Gly Gly Gly Gly Gly Gly Gly Gly Gly Gly Gly Gly
65                 70                 75                 80
Gly Gly Gly Gly Gly Gly Gly Gly Gly Gly Gly Gly Gly Gly Gly
               85                 90                 95
Gly Gly Gly Gly Gly Gly Gly Gly Gly Gly Gly Gly Gly Gly Gly
           100                105                110
Gly Gly Gly Gly Gly Gly Gly Gly Gly Gly Gly Gly Gly Gly Gly
       115                120                125
Gly Gly Gly Gly Gly Gly Gly Gly Gly Gly Gly Gly Gly Gly Gly
   130                135                140
Gly Gly Gly Gly Gly Gly Gly Gly Gly Gly Gly Gly Gly Gly Gly
145                150                155                160
Gly Gly Gly Gly Gly Gly Gly Gly Gly Gly Gly Gly Gly Gly Gly
               165                170                175
Gly Gly Gly Gly Gly Gly Gly Gly Gly Gly Gly Gly Gly Gly Gly
           180                185                190
Gly Gly Gly Gly Gly Gly Gly Gly
        195                200
```